US007403808B2

(12) United States Patent
Istvan et al.

(10) Patent No.: US 7,403,808 B2
(45) Date of Patent: Jul. 22, 2008

(54) WIRELESS ECG SYSTEM

(75) Inventors: Rud Istvan, Fort Lauderdale, FL (US); Bill Gregory, Fort Lauderdale, FL (US); Kenneth Solovay, Weston, FL (US); David Paul Chastain, Acton, MA (US); John David Gundlach, Acton, MA (US); Nicholas C. Hopman, Lake Zurich, IL (US); Daniel L. Williams, Norwell, MA (US); Franco Lodato, Weston, FL (US); Michael Salem, Ft. Lauderdale, FL (US)

(73) Assignee: LifeSync Corporation, Ft. Lauderdale, FL (US)

( * ) Notice: Subject to any disclaimer, the term of this patent is extended or adjusted under 35 U.S.C. 154(b) by 133 days.

(21) Appl. No.: 11/077,934

(22) Filed: Mar. 11, 2005

(65) Prior Publication Data

US 2005/0177052 A1 Aug. 11, 2005

Related U.S. Application Data

(63) Continuation of application No. 09/998,733, filed on Nov. 30, 2001, now Pat. No. 7,197,357, which is a continuation-in-part of application No. 09/908,509, filed on Jul. 17, 2001, now Pat. No. 6,611,705.

(51) Int. Cl.
*A61B 5/0408* (2006.01)
*H01R 29/00* (2006.01)

(52) U.S. Cl. ........................ 600/393; 600/509; 439/188

(58) Field of Classification Search ......... 600/508–509, 600/384–397, 300, 301, 481, 529, 545, 286–294; 128/901–904; 439/188–189; 607/5, 142, 607/149, 152; D24/184–187, 167–168
See application file for complete search history.

(56) References Cited

U.S. PATENT DOCUMENTS

| | | | |
|---|---|---|---|
| 3,199,508 | A | 8/1965 | Roth |
| 3,603,881 | A | 9/1971 | Thornton |
| 3,639,907 | A | 2/1972 | Greatbatch |
| 3,757,778 | A | 9/1973 | Graham |
| 3,774,594 | A | 11/1973 | Huszar |

(Continued)

FOREIGN PATENT DOCUMENTS

EP 0212278 A2 3/1987

(Continued)

OTHER PUBLICATIONS

Neukomm, Peter A., A Radio-Controlled Monitoring System for Multichannel Telemetry, Biotelemetry, 1974, pp. 251-263, vol. 1.

(Continued)

*Primary Examiner*—Kennedy J. Schaetzle
*Assistant Examiner*—Jessica L. Reidel
(74) *Attorney, Agent, or Firm*—Michael J. Keller; Lott & Friedland, P.A.

(57) ABSTRACT

A cardiac monitoring system that detects electrical signals from a patient's heart and wirelessly transmits the signals digitally to a remote base station via telemetry. The base station converts the digital signals back to analog electrical signals that can be read by an electrocardiograph (ECG) monitor.

14 Claims, 13 Drawing Sheets

U.S. PATENT DOCUMENTS 3,830,228 A 8/1974 Foner
3,834,373 A 9/1974 Sato
3,910,260 A 10/1975 Samoff et al.
3,925,611 A 12/1975 Dennis
3,986,498 A 10/1976 Lewis
4,042,906 A 8/1977 Ezell
4,121,573 A 10/1978 Crovella et al.
4,150,284 A 4/1979 Trenkler et al.
4,173,971 A 11/1979 Karz
4,186,749 A 2/1980 Fryer
4,280,507 A * 7/1981 Rosenberg .................. 600/508
4,281,664 A 8/1981 Duggan
4,353,372 A * 10/1982 Ayer .......................... 600/393
4,407,298 A * 10/1983 Lentz et al. ................. 600/526
4,441,498 A 4/1984 Nordling
4,556,063 A 12/1985 Thompson et al.
4,562,840 A 1/1986 Batina et al.
4,583,549 A 4/1986 Manoli
4,586,508 A 5/1986 Batina et al.
4,606,352 A 8/1986 Geddes et al.
4,681,118 A 7/1987 Asai et al.
4,709,704 A 12/1987 Lukasiewicz
4,747,413 A 5/1988 Bloch
4,763,660 A * 8/1988 Kroll et al. .................. 600/391
4,784,162 A 11/1988 Ricks et al.
4,791,933 A 12/1988 Asai et al.
4,803,625 A 2/1989 Fu et al.
4,832,608 A * 5/1989 Kroll ........................... 439/67
4,883,064 A 11/1989 Olson et al.
4,889,131 A 12/1989 Salem et al.
4,909,260 A * 3/1990 Salem et al. ................ 600/534
4,957,109 A 9/1990 Groeger et al.
4,966,154 A 10/1990 Cooper et al.
4,974,607 A 12/1990 Miwa
4,981,141 A 1/1991 Segalowitz
5,012,411 A 4/1991 Policastro et al.
5,025,808 A 6/1991 Hafner
5,036,869 A 8/1991 Inahara
5,085,224 A 2/1992 Galen et al.
5,113,869 A 5/1992 Nappholz et al.
5,131,399 A 7/1992 Sciarra
5,153,584 A 10/1992 Engira
5,168,874 A 12/1992 Segalowitz
5,176,676 A * 1/1993 Kurtze ......................... 606/32
5,181,519 A 1/1993 Bible
5,203,720 A * 4/1993 Zini ........................... 439/502
5,224,479 A 7/1993 Sekine
5,226,431 A 7/1993 Bible et al.
5,238,001 A 8/1993 Gallant et al.
5,307,818 A 5/1994 Segalowitz
5,309,920 A 5/1994 Gallant et al.
5,327,888 A * 7/1994 Imran ......................... 600/393
5,348,008 A 9/1994 Bornn et al.
5,394,882 A 3/1995 Mawhinney
5,400,794 A 3/1995 Gorman
5,417,222 A 5/1995 Dempsey et al.
5,458,122 A 10/1995 Hethuin
5,458,124 A 10/1995 Stanko et al.
5,464,021 A 11/1995 Birnbaum
5,491,474 A 2/1996 Suni et al.
5,511,553 A * 4/1996 Segalowitz .................. 600/508
5,522,396 A 6/1996 Langer et al.
5,524,362 A * 6/1996 Quandt et al. ................. 34/526
5,524,637 A 6/1996 Erickson
5,538,007 A 7/1996 Gorman
5,546,950 A * 8/1996 Schoeckert et al. ......... 600/508
5,549,113 A 8/1996 Halleck et al.
5,579,001 A 11/1996 Dempsey et al.
5,579,781 A 12/1996 Cooke
5,628,324 A 5/1997 Sarbach
5,634,468 A 6/1997 Platt et al.
5,685,303 A * 11/1997 Rollman et al. ............. 600/390
5,690,119 A 11/1997 Rytky et al.
5,694,940 A 12/1997 Unger et al.
5,718,234 A 2/1998 Warden et al.
5,720,771 A 2/1998 Snell
5,748,103 A 5/1998 Flach et al.
5,755,230 A 5/1998 Schmidt et al.
5,759,199 A 6/1998 Snell et al.
5,767,791 A 6/1998 Stoop et al.
5,855,550 A 1/1999 Lai et al.
5,862,803 A 1/1999 Besson et al.
5,865,733 A 2/1999 Malinouskas et al.
5,873,369 A 2/1999 Laniado et al.
5,882,300 A 3/1999 Malinouskas et al.
5,899,928 A 5/1999 Sholder et al.
5,899,931 A 5/1999 Deschamp et al.
5,907,291 A 5/1999 Chen et al.
5,913,827 A 6/1999 Gorman
5,919,141 A 7/1999 Money et al.
5,931,791 A 8/1999 Saltzstein et al.
5,944,659 A 8/1999 Flach et al.
5,949,352 A 9/1999 Ferrari
5,957,854 A 9/1999 Besson et al.
5,959,529 A 9/1999 Kail, IV
5,964,701 A 10/1999 Asada et al.
5,966,692 A 10/1999 Langer et al.
6,010,359 A * 1/2000 Etters et al. ................. 439/496
6,047,201 A 4/2000 Jackson, III
6,073,046 A 6/2000 Patel et al.
6,083,248 A 7/2000 Thompson
6,093,146 A 7/2000 Filangeri
6,102,856 A 8/2000 Groff et al.
6,142,949 A * 11/2000 Ubby ......................... 600/508
6,149,602 A 11/2000 Arcelus
6,198,394 B1 3/2001 Jacobsen et al.
6,213,942 B1 4/2001 Flach et al.
D443,063 S * 5/2001 Pisani et al. ............... D24/187
6,225,901 B1 5/2001 Kail, IV
6,238,338 B1 5/2001 DeLuca et al.
6,287,252 B1 * 9/2001 Lugo .......................... 600/300
6,304,774 B1 10/2001 Gorman
6,415,169 B1 * 7/2002 Kornrumpf et al. ......... 600/382
6,416,471 B1 7/2002 Kumar et al.
6,441,747 B1 8/2002 Khair et al.
6,450,953 B1 9/2002 Place et al.
6,453,186 B1 * 9/2002 Lovejoy et al. ............. 600/386
6,480,733 B1 11/2002 Turcott
6,496,705 B1 12/2002 Ng et al.
6,526,310 B1 * 2/2003 Carter et al. ................ 600/509
6,611,705 B2 * 8/2003 Hopman et al. ............. 600/509
6,970,737 B1 11/2005 Brodnick et al.
7,197,357 B2 * 3/2007 Istvan et al. ................. 600/509
2002/0072682 A1 * 6/2002 Hopeman et al. ........... 600/509
2005/0206518 A1 9/2005 Welch et al.
2005/0228299 A1 10/2005 Banet
2005/0228300 A1 10/2005 Jaime et al.
2005/0261594 A1 11/2005 Banet
2005/0267381 A1 12/2005 Benditt et al.
2005/0277841 A1 12/2005 Shennib
2006/0030760 A1 2/2006 Geiger
2006/0047214 A1 3/2006 Fraden
2006/0047447 A1 3/2006 Brady et al.
2006/0100531 A1 5/2006 Moser
2006/0122528 A1 6/2006 Gal
2006/0142648 A1 6/2006 Banet et al.
2006/0155173 A1 7/2006 Anttila et al.
2006/0178617 A1 8/2006 Adams et al.

FOREIGN PATENT DOCUMENTS

EP 10068871 B1 10/2005
EP 1676524 A1 7/2006
GB 2271691 4/1994

| | | | |
|---|---|---|---|
| WO | WO9718639 | | 5/1997 |
| WO | WO9749077 | | 12/1997 |
| WO | WO9800056 | | 1/1998 |
| WO | WO2005104930 | A1 | 11/2005 |
| WO | WO2005122883 | A2 | 12/2005 |
| WO | WO2006008740 | A1 | 1/2006 |
| WO | WO2006009767 | A1 | 1/2006 |
| WO | WO2006018833 | A2 | 2/2006 |
| WO | WO2006029322 | A2 | 3/2006 |
| WO | WO2006039752 | A1 | 4/2006 |
| WO | WO2006050206 | A1 | 5/2006 |
| WO | WO2006064397 | A2 | 6/2006 |
| WO | WO2006076498 | A2 | 7/2006 |

OTHER PUBLICATIONS

Kimmich, H.P. and Vos, J.A., Telemetry of Respiratory Air Flow, Biotelemetry International Symposium, May 5-8, 1971, pp. 111-120, Meander N.V., Netherlands.
Kimmich, H.P. and Vos, J.A., Single to Seven Channel Lightweight Biotelemetry System, Biotelemetry International Symposium, May 5-8, 1971, pp. 57-64, Meander N.V., Netherlands.
Kimmich, H.P. and Ijsenbrandt, H.J.B., Personal PDM/PCM Biotelemetry System, Biotelemetry II Second International Symposium, May 20-24, 1974, pp. 2-4, S. Karger, Basel.
Kimmich, H.P., Clinical Telemetry and Patient Monitoring, Biotelemetry II Second International Symposium, May 20-24, 1974, pp. 190-195, S. Karger, Basel.
Kimmich, H.P. and Kreuzer, F., Trends in Biomedical Telemetry and Patient Monitoring, Date Unknown, pp. E2-7(1)-(2).
Kimmich, H.P., Biotelemetry, Encyclopedia of Medical Devices and Instrumentation, 1988, pp. 409-425, vol. 1., John Wiley & Sons, USA.
Kimmich, H.P., Modern Patient Care Using Biotelemetry: It's Potential and Technical Realization at Present and in the Future, Medical Progress Through Technology, 1982, pp. 85-93, vol. 9, No. 2/3, Springer-Verlag.
Skutt, H.R., Fell, R.B. and Hagstrom, E.C., The Use of Telemetry to Obtain Physiological Data During Exercise, Biotelemetry International Symposium, May 5-8, 1971, pp. 21-29, Meander N.V., Netherlands.
Ivison, J.M., Hoare D.W. and Qazi, S., A Time-Division Multiplexed Telemetry System Using Delta-Modulation, Biotelemetry International Symposium, May 5-8, 1971, pp. 39-48.
Zerzawy, R. and Bachmann, K., A Programmable Four Channel System for Long-Term Radio Telemetry of Biomedical Parameters, Biotelemetry International Symposium, 1971, pp. 49-56.
Ijsenbrandt, H.J.B., Kimmich, H.P. and Van Den Akker, A.J., Single to Seven Channel Lightweight Biotelemetry System, Biotelemetry International Symposium, 1971, pp. 57-64.
Klein, M., Milhaud, C. and Rebelle, J., Development an Adjustment of a Multi-Channel Miniaturized FM/AM Telemetering System Adapted to Primates, Biotelemetry International Symposium, May 5-8, 1971, pp. 83-88.
Kocnar, K. and Vichr, R., Mobile Telemetric Equipment for the Transmission of ECG and Respiratory Frequency With Automatic Data Recording, Biotelemetry International Symposium, May 5-8, 1971, pp. 95-98.
Kimmich, H.P., Oxygen Consumption Measurements During Exercise By Means of Radiotelemetry, Biotelemetry International Symposium, May 5-8, 1971, pp. 130-136.
Gachmann, K. and Zerzawy, R., Radiotelemetry of Direct Blood Pressure Movements in Aorta, Pulmonary Artery and Heart, Biotelemetry International Symposium, 1971, p. 183, 186-7.
Furukawa, T. Tsuchida, Y., Matsumoto, G. and Shigezumi, M., Technical Improvements in Radiotelemetering of the Electrocardiogram, Biotelemetry International Symposium, May 5-8, 1971, pp. 202-215.
Wilson-Davies, C.C., Multi-Channel Telemetry of Cardiovascular Data, Biotelemetry International Symposium, May 5-8, 1971, pp. 234-236.
Castelfiori, S. and Dubini, S., Radiotelemetry System For Fetal Monitoring, Biotelemetry International Symposium, May 5-8, 1971, pp. 237-245.
Kozinski, E., Estimation of the Intensity of Physical Exercises in Children and Adolescents Based on Telemetric Studies of Circulatory System, Biotelemetry International Symposium, May 5-8, 1971, pp. 251-255.
Rous, J. and Kocnar, K., Telemetrical Measurements During Sport Performance on Sportsmen with Cardiac Arrhythmias, Biotelemetry International Symposium, 1971, pp. 256-263.
Vos, J.A. and Kimmich, H.P., Telemetry of Biomechanical Forces During Exercise, Biotelemetry International Symposium, May 5-8, 1971, pp. 279-288.
Kristan, L., Dvorak, M., Zacek, I. and Pokorny, F., Experience With the Application of Biotelemetry (ECG, EMG) Under Strenuous Working Conditions in Various Operational Environments, Biotelemetry International Symposium, May 5-8, 1971, pp. 289-297.
Wagner, G., Hrynczuk, J.R. and Nielsen, J.F., EMG From Smooth Musculature (Uterus, Ureter, Gut) in Unrestrained Animals Monitored by Telemetry, Biotelemetry International Symposium, May 5-8, 1971, pp. 298-304.
Stalberg, E. and Kaiser, E., Long-Term EEG-Telemetry, Biotelemetry International Symposium, May 5-8, 1971, pp. 307-316.
Currie, J.C.M., Riddle, H.C. and Watson, B.W., The Use of Telemetry to Study the Physiological and Clinical Variations of Intracranial Pressure in Man, Biotelemetry International Symposium, May 5-8, 1971, pp. 326-331.
Sandler, H., Fryer, T.B. and Westbrook, R.M., Single and Multichannel Implanted Telemetry Systems, Biotelemetry International Symposium, May 5-8, 1971, pp. 345-352.
Evans, B.T., A Remotely Operated ECG Telemeter for Chronic Implantation in Rats, Biotelemetry International Symposium, May 5-8, 1971, pp. 353-359.
Nielsen, J.F. and Wagner, G., Implantable FM-Telemetry Transmitters For Registration of Biopotentials, Biotelemetry International Symposium, May 5-8, 1971, pp. 360-364.
Voegeli, F. and Kraft, W., Multichannel Telemetry of Physiological Parameters (Body Temperature, ECG, EEG) in the Rat: I. Design and Methods, Biotelemetry International Symposium, May 5-8, 1971, pp. 371-380.
Borbely, A. A., Baumann, I. and Waser, N.M., Multichannel Telemetry of Physiological Parameters (Body Temperature, EKG, EEG) in the Rat: II. Applications in Neuropharmacology, Biotelemetry International Symposium, May 5-8, 1971, pp. 381-388.
Pircher, L.A., Telemetry of Cardiovascular Parameters on Fighter Aircraft Flying Pilots, Biotelemetry Internationals Symposium, May 5-8, 1971, pp. 406-411.
Cook, T., Fernald, K.W., Miller, T.K. and Paulos, J.J., A Custom Microprocessor for Implantable Telemetry Systems, Third Annual IEEE Symposium on Computer-Based Medical Systems, Jun. 3-6, 1990, pp. 412-417.
Fernald, K.W., Stackhouse, B.A., Paulos, J.J. and Miller, T.K., A System Architecture for Intelligent Implantable Biotelemetry Instruments, Proceedings of the Annual International Conference of the IEEE Engineering in Medicine and Biology Society, Nov. 9-12, 1989, vol. 11, pp. 1411-1412.
Fernald, K.W., Cook, T.A., Miller III, T.K. and Paulos, J.J., A Microprocessor-Based Implantable Telemetry System, Computer, Mar. 1991, pp. 23-30.
Stackhouse, B.A., Thesis: A Transmitter Circuit Design for an Implantable Biomedical Chip Set, North Carolina State University, 1989.
Powers, C.C., Thesis: A Base Station Receiver for Biomedical Telemetry, North Carolina State University, 1991.
Fernald, K.W., Thesis: A Microprocessor-Based System for the Fast Prototyping of Implantable Instruments for Biomedical Research Applications, North Carolina State Univ., 1992.

* cited by examiner

FIG.9A
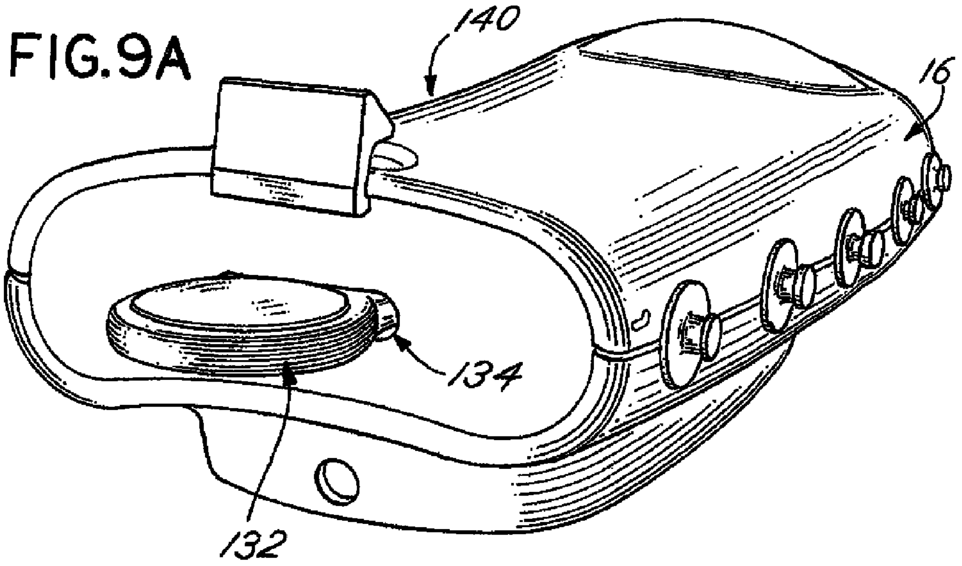
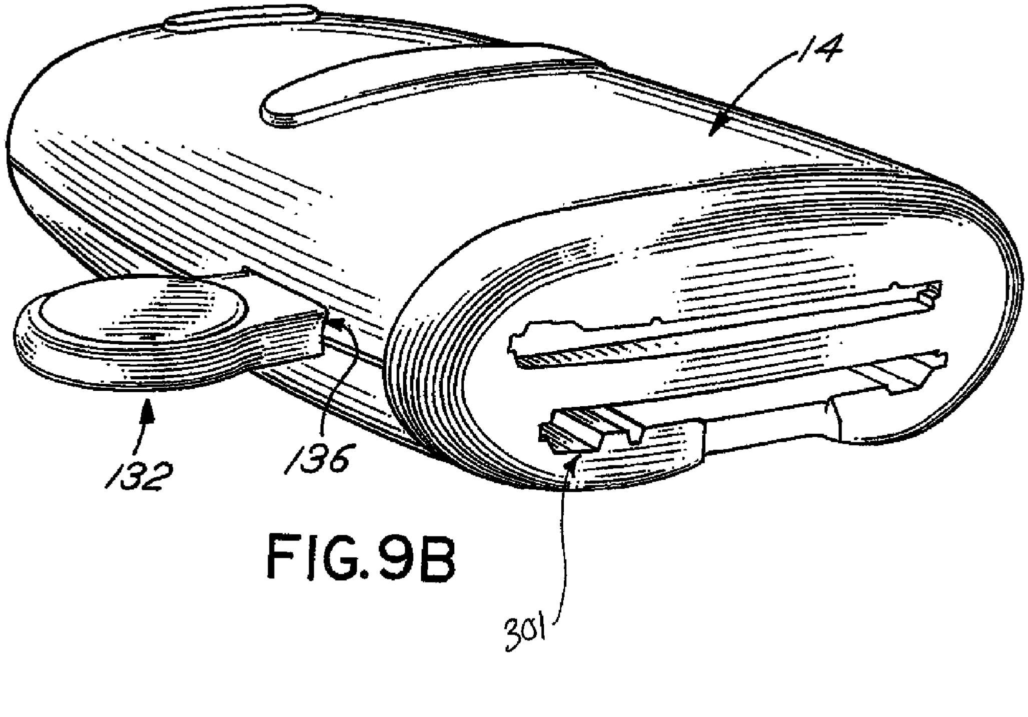
FIG.9B

WIRELESS ECG SYSTEM

RELATED APPLICATIONS

This application is a continuation of application Ser. No. 09/998,733, filed Nov. 30, 2001, now U.S. Pat. No. 7,197,357, which is a continuation-in-part of application Ser. No. 09/908,509, filed Jul. 17, 2001, U.S. Pat. No. 6,611,705, the disclosure and contents of which are incorporated herein by reference. Application Ser. No. 09/908,509 and the claimed invention were made by or on the behalf of GMP Wireless Medicine, Inc., now LifeSync Corporation upon change in corporate name, and Motorola, Inc., as parties to a joint research agreement, within the meaning of 35 U.S.C. §103 (c), that was in effect on or before the date the claimed invention was made.

A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF THE INVENTION

The present invention relates to a cardiac monitoring system and, more particularly, to a wireless electrocardiograph (ECG) system.

BACKGROUND OF THE INVENTION

An electrocardiograph (ECG) system monitors heart electrical activity in a patient. Conventional ECG systems utilize conductive pads or electrodes placed on a patient in specific locations to detect electrical impulses generated by the heart during each beat. In response to detection of the electrical impulses from the heart, the electrodes produce electrical signals indicative of the heart activity. Typically, these electrical signals are directly transferred from the electrodes to a stationary ECG monitor via multiple cables or wires. The ECG monitor performs various signal processing and computational operations to convert the raw electrical signals into meaningful information that can be displayed on a monitor or printed out for review by a physician.

Doctors have used ECG systems to monitor a patient's heart activity for decades. Currently, there are several different systems that use ECG signals to monitor a patient's heart activity. These systems, however, are generally stationary and are not developed or suitable for portable use. While portable telemetry systems exist, they are not a direct replacement for stationary ECG monitors. Moreover, because conventional systems use multiple cables or wires, and are cumbersome and uncomfortable for the patient, and require a significant amount of set up time. Thus, a need exists for an ECG system that solves the aforementioned problems.

BRIEF SUMMARY OF THE INVENTION

The present invention relates to a wireless ECG system that is universally compatible with existing or conventional ECG monitors. The ECG system comprises a chest assembly, a body electronics unit, and a base station. The chest assembly connects to electrodes specifically located on a patient's body for detecting electrical signals from the patient's heart. The electrical signals are detected by the chest assembly—thus, providing up to a "7 lead" analysis of the heart. Alternatively, the chest assembly can be augmented with a precordial assembly that connects to electrodes specifically located on the patient's body—thus, providing a "12 lead" analysis of the heart.

The electrical signals are transmitted through the chest assembly and the precordial assembly to the body electronics unit, which removably secures to the patient via an armband. The body electronics unit transmits the electrical signals to the base station via radio transmission. The base station transmits the electrical signals to a conventional ECG monitor via standard cabling, which, in turn, processes or transforms the electrical signals into meaningful information that can be displayed on the ECG monitor for review by a physician.

The ECG system eliminates the wires that ordinarily tethers an ECG patent to an ECG monitor by replacing conventional wires with a radio link. The present invention is lightweight and portable—thereby providing increased comfort and mobility to the patient. In addition, the present invention requires decreased setup times and is more convenient for health practitioners to use than conventional ECG systems.

These as well as other novel advantages, details, embodiments, features, and objects of the present invention will be apparent to those skilled in the art from the following detailed description of the invention, the attached claims and accompanying drawings, listed herein below which are useful in explaining the invention.

BRIEF DESCRIPTION OF THE DRAWING

The foregoing aspects and many of the advantages of the present invention will become readily appreciated by reference to the following detailed description of the preferred embodiment, when taken in conjunction with the accompanying drawings, wherein:

FIG. 9*a* is a perspective view of an exemplary embodiment of the base station used in conjunction with the token key;

FIG. 9*b* depicts the body electronics unit used in conjunction with the token key;

DESCRIPTION OF THE PREFERRED EMBODIMENT

Figure 1:
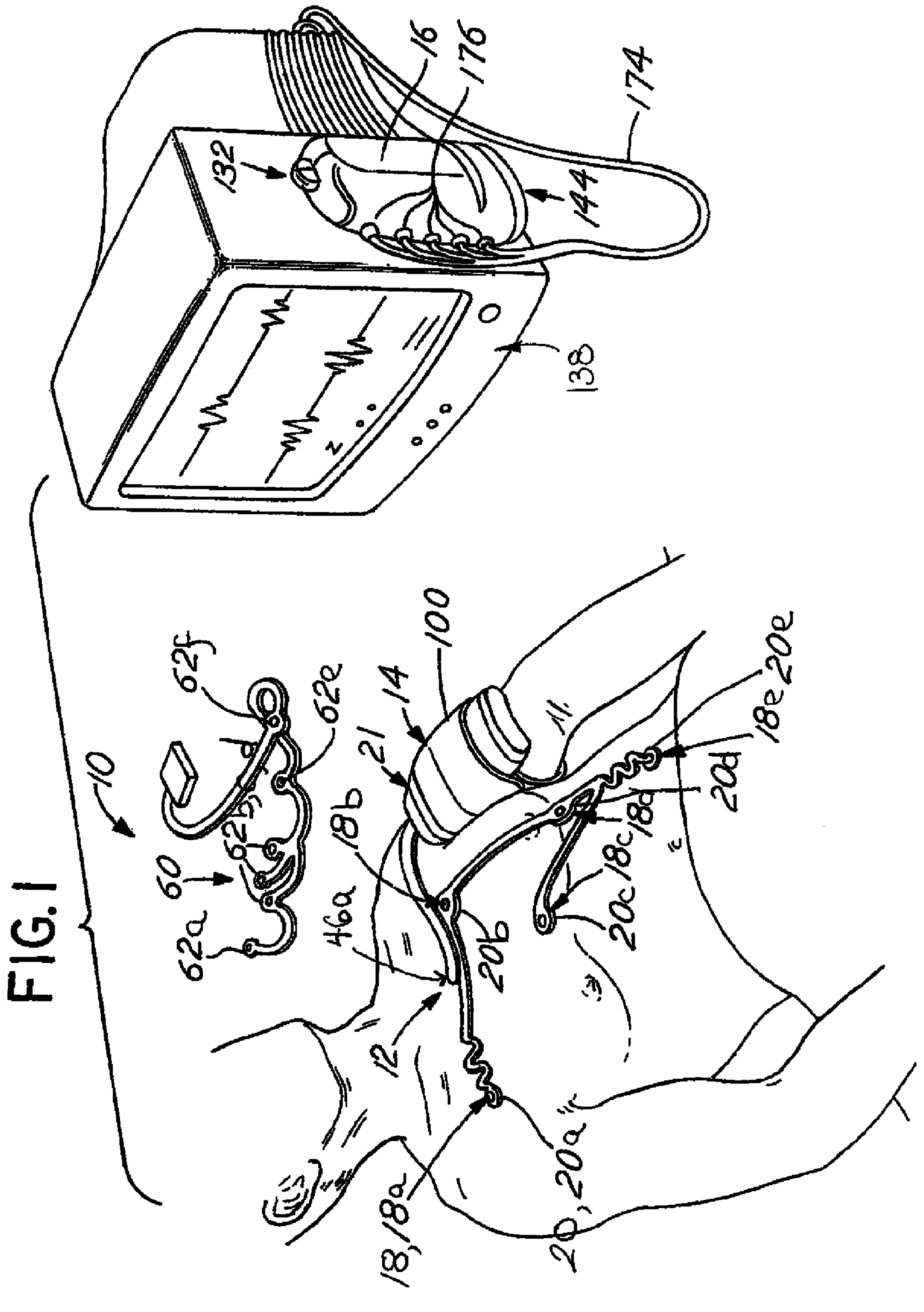
FIG. 1 is a perspective view of an exemplary embodiment of the ECG system.

For a better understanding of the present invention, reference may be had to the following detailed description taken in conjunction with the appended claims and accompanying drawings. Briefly, the present invention relates to a wireless, portable ECG system. Referring to FIG. 1, the ECG system 10 comprises a chest assembly 12, a body electronics unit 14, and a base station 16.

The chest assembly 12 is a one-piece flexible circuit that connects a plurality of electrode connectors 18, which are individually labeled 18*a*, 18*b*, 18*c* 18*d*, and 18*e*. The electrode connectors 18 have releasable connections that connect to electrodes 20, which are individually labeled 20*a*, 20*b*, 20*c*, 20*d*, and 20*e*. Preferably, the electrode connectors 18 have snap terminals that connect to electrodes 20 having snap terminals. Each electrode connector 18 connects to an electrically conductive element or trace for transmitting electrical signals. The electrically conductive elements or traces run along the chest assembly 12 and connect to a chest assembly connector 21.

Figure 2:
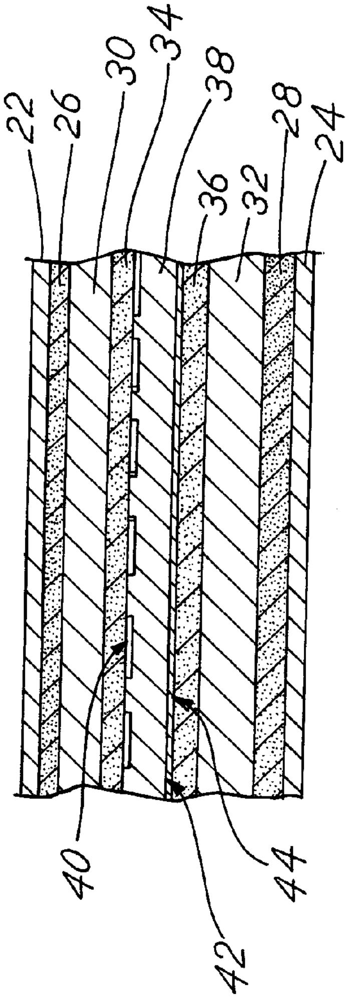
FIG. 2 is a cross sectional view of the chest assembly and the precordial assembly.

Referring to FIG. 2, the chest assembly 12 has outer layers 22, 24 that are constructed of a lightweight and reasonably moisture resistant material, such as DuPont Sontara® or other suitable fabric. Adhesive layers 26, 28 secure insulating layers 30, 32 to the outer layers 22, 24 respectively. Insulating layers 30, 32 are constructed of Mylar® (polyester) film or other suitable insulating material. Adhesive layers 34, 36 secure the insulating layers 30, 32 to a base layer 38. The base layer 38 is preferably constructed of Mylar film and has a first side 40 and a second side 42. The electrically conductive elements or traces that connect to the electrode connectors 18 are located on the first side 40 of the base layer 38. One such conductive element or trace is shown at 39. A shielding layer 44 for reducing any external inferences or radio frequency noise with the chest assembly 12 is located on the second side 42 of the base layer 38. The shielding layer 44 may be constructed of single or multiple layers of dielectric, or electrically or magnetically conductive material. The back of the electrode connector 18 may also be covered with Mylar to further insulate the chest assembly 12 and prevent an externally applied electric potential from entering the ECG system. The shielding layer preferably comprises an X-patterned grid.

Referring back to FIG. 1, the chest assembly 12 attaches to five electrodes 20 and provides a means for generally positioning the electrodes on the patient, thereby providing up to a "7 lead" analysis of the electrical activity of the heart. The electrode connectors 18 are preferably labeled and color-coded to ensure that the chest assembly 12 is properly positioned on the patient and connected to the appropriate electrodes 20. For instance, the electrode connectors 18*a*, 18*b*, 18*c*, 18*d*, 18*e* are labeled RL, LA, LL, RA, and V, respectively. The chest assembly 12 is constructed such that the RA electrode connector is connected to an electrode positioned on the right side of the patient's chest about level of the first and second intercostal space, the LA electrode connector is connected to an electrode positioned on the left side of the patient's chest about level of the first and second intercostal space, the RL and LL electrode connectors are connected to electrodes positioned on the left side of the patient's torso, and the V electrode connector is connected to an electrode positioned in the middle of the patient's chest about level of the fourth and fifth intercostal space. The chest assembly 12 is designed such that it is centered on the chest below the patient's clavicle.

Figure 3:
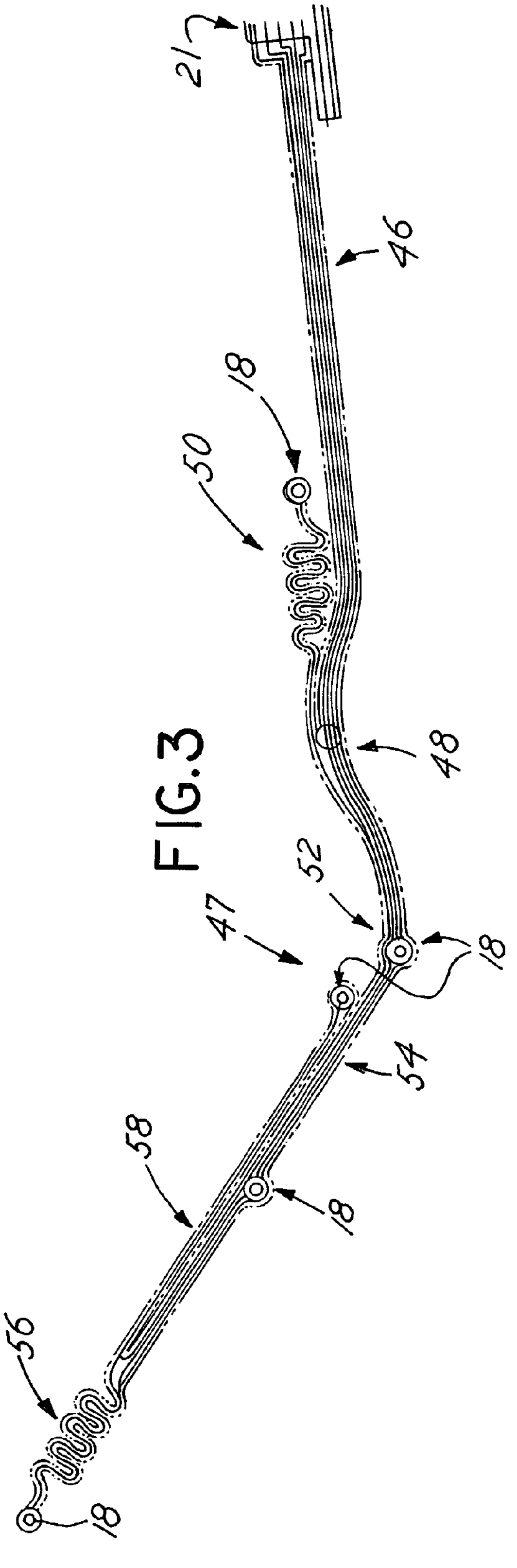
FIG. 3 is a top view of an exemplary embodiment of the chest assembly.

Referring to FIG. 3, the chest assembly 12 is configured to provide flexible positioning of the chest assembly 12 on the patient. FIG. 3 is for illustrative purposes only, and thus, the chest assembly 12, as depicted in FIG. 3, is not limited to any particular shape or configuration. The chest assembly 12 has a linear section or tail 46 extending from the chest assembly connector 21. Referring back to FIG. 1, the tail 46 has a securing means 46*a* which allows the tail 46 to extend to either side of the patient. This securing means 46*a* may be any suitable mechanical device although adhesive or a clip is most preferred. Referring back to FIG. 3, the tail 46 flows into an electrode retaining section 47. The electrode retaining section 47 has an arcuate section 48. A first expandable arm 50 attaches to the arcuate section 48. The RA electrode connector attaches to the first expandable arm 50. The arcuate section 48 flows into a transition section 52. The LA electrode connector attaches to the transition section 52. The transition section 52 flows into a linear run 54. The RL electrode connector attaches to the linear run 54. A second expandable arm 56 and an extension arm 58 attach to the linear run 54. The V electrode connector attaches to the second extension arm 58 and the LL electrode connector attaches to the second expandable arm 56.

The expandable arms 50, 56 are die cut in a serpentine pattern. The expandable arms 50, 56 comprise polypropylene or polyethylene fabric, Kapton, Mylar, or other flexible, memoryless material. The expandable arms 50, 56 expand, if necessary, by elongating the serpentine pattern. When expanded, a portion or all of the expandable arm is extended. Where only a portion of the expandable arm is extended, another portion remains folded. The expandable arms 50, 56 allow for extension as needed to so that the chest assembly 12 can fit patients of various sizes and also allow for patient movement when the patient is wearing the chest assembly 12. The extension arm 58 allows for flexible positioning of the V electrode connector in the middle of the patient's chest such as placement at electrode position V1, V2 or V3. In some instances, the health care practitioner may desire not to utilize the extension arm 58 for taking electrocardiograph measurements. Thus, to keep the extension arm 58 secured to the linear run 58 and to ensure that the extension arm 58 will not interfere with the placement and positioning of the chest assembly 12, the extension arm 58 is die cut with a perforated seam that connects the extension arm 58 and the linear run 54 along the length of the extension arm 58. If the health care practitioner desires to use the extension arm 58, the perforated seam is unbroken so that the extension arm 58 can be selectively positioned on the patient's chest.

The chest assembly 12 can be used with a precordial assembly 60 to provide a "12-lead" analysis of the electrical activity of the heart. Similar to the chest assembly 12, the precordial assembly 60 is a one-piece flexible circuit that connects a plurality of electrode connectors 62. The electrode connectors 62 have releasable connections that connect to electrodes 64. Preferably, the electrode connectors 62 have snap terminals that connect to electrodes 64 having snap terminals. Each electrode connector 62 connects to an electrically conductive element or trace for transmitting electrical signals from a patient's heart. The electrically conductive elements or traces run along the precordial assembly 60 and connect to a precordial assembly connector 66. The precordial assembly 60 has the construction as shown in FIG. 2.

As depicted in FIG. 1, the precordial assembly 60 attaches to six electrodes 64 (not shown) that are selectively positioned on the abdomen and middle chest of the patient. The electrode connectors 62 of the precordial assembly 60 are preferably labeled and color-coded so as to prevent a health care provider from applying or positioning the precordial assembly onto the patient improperly. For instance, the electrode connectors 62*a*, 62*b*, 62*c*, 62*d*, 62*e*, and 62*f* are labeled V1, V2, V3, V4, V5, and V6, respectively. When the precordial assembly 60 is used, the V electrode connector on the chest assembly 12 is removed from its electrode and replaced with an electrode connector on the precordial assembly 60.

Figure 4:
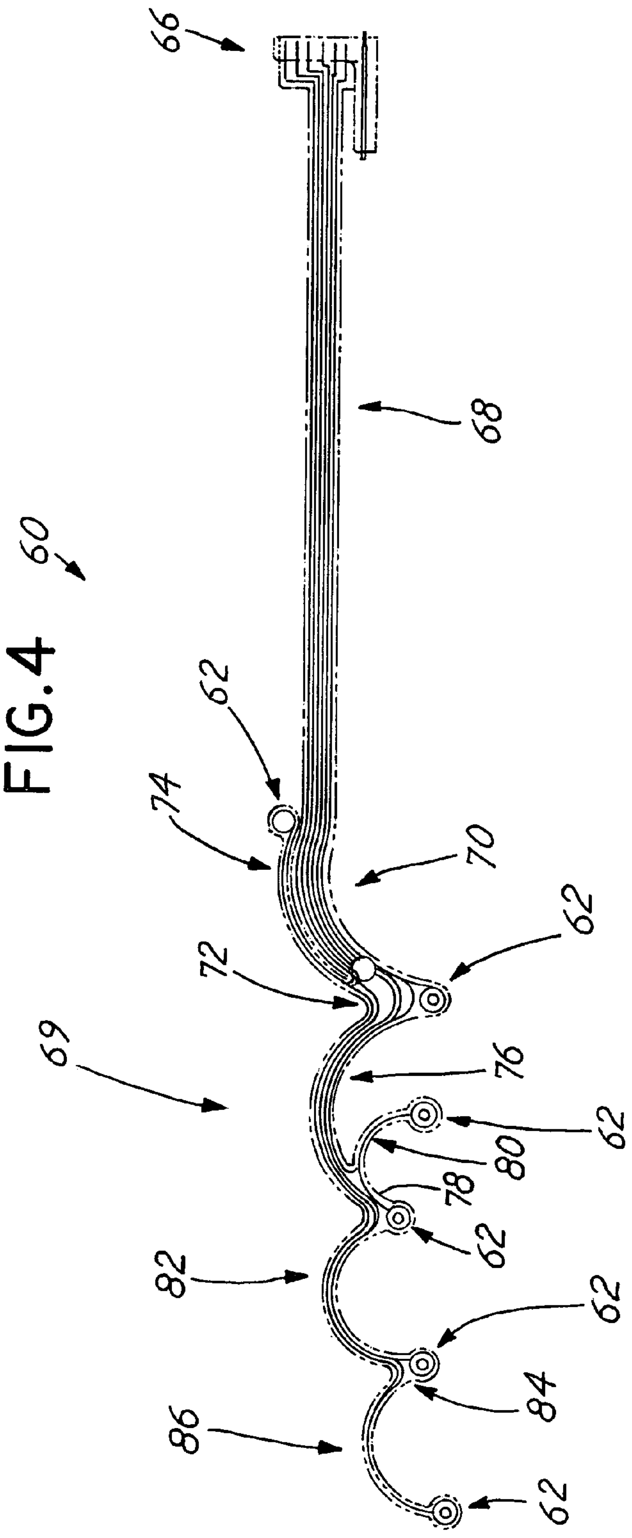
FIG. 4 is a top view of an exemplary embodiment of the precordial assembly.

As shown in FIG. 4, the precordial assembly 60 is configured to provide flexible positioning of the precordial assembly 60 on the patient. FIG. 4 is for illustrative purposes only, and thus, the precordial assembly 60, as depicted in FIG. 4, is not limited to any particular shape or configuration. The precordial assembly has a linear section or tail 68 extending from the precordial assembly connector 66. The linear section or tail 68 flows into an electrode retaining section 69. The electrode retaining section 69 has a first arcuate section 70 having a first transition section 72. The V2 electrode connector attaches to the first transition section 72. The V1 electrode connector attaches to a first extension arm 74 connected to the first transition section 72. A second arcuate section 76 extends from the first transition section 72. A second transition section 78 abuts the second arcuate section 76 and the V4 electrode connector attaches to the second transition section 76. The V3 electrode connector attaches to a second extension arm 80 connected the second transition section 78. A third arcuate section 82 flows from the second transition section 78. The third arcuate section 82 abuts a third transition section 84. The V5 electrode connector attaches to the third transition section 84. A fourth arcuate section 86 extends from the third transition section 84. The V6 electrode attaches to the fourth arcuate section 86. The configuration of the precordial assembly 60 allows the health care provider or physician to flexibly position the electrode connectors 62 as needed to properly situate the precordial assembly 60 on the patient and to allow for patient movement when the patient is wearing the precordial assembly 60

In operation, the chest assembly 12 and the precordial assembly 60 detect electrical signals generated by the heart during each beat and transfer these signals to the body electronics unit 14. When the system is operating in "7 lead" mode (i.e. when only the chest assembly 12 is being used) the body electronics unit 14 acquires signals from the RL, RA, LL, LA, and V electrodes. The body electronics unit 14 uses the RL electrode as a ground reference. When the system is operating in the "12 lead" mode (i.e. the chest assembly 12 and the precordial assembly 60 are being used) the body electronics unit 14 acquires signals from the RL, RA, LL, and LA electrodes via the chest assembly 12 and acquires signals from the V1, V2, V3, V4, V5, and V6 electrodes via the precordial assembly 60. Alternatively, a various number of electrodes may be monitored by the system. For example, the health care provider or physician may choose to use only two electrodes to monitor the heart, seven electrodes to monitor the heart, or the like. In other words, the present system is not limited to performing a "7 lead" and "12 lead" analysis of the heart. In addition, to detecting electrical signals from the heart, the chest assembly 12 and the precordial assembly 60 may be constructed to detect other vital signs of the patient, for example, pulse, respiration rate, heart rate, temperature EEG signals, and pulse oximeter signals.

Figure 5:
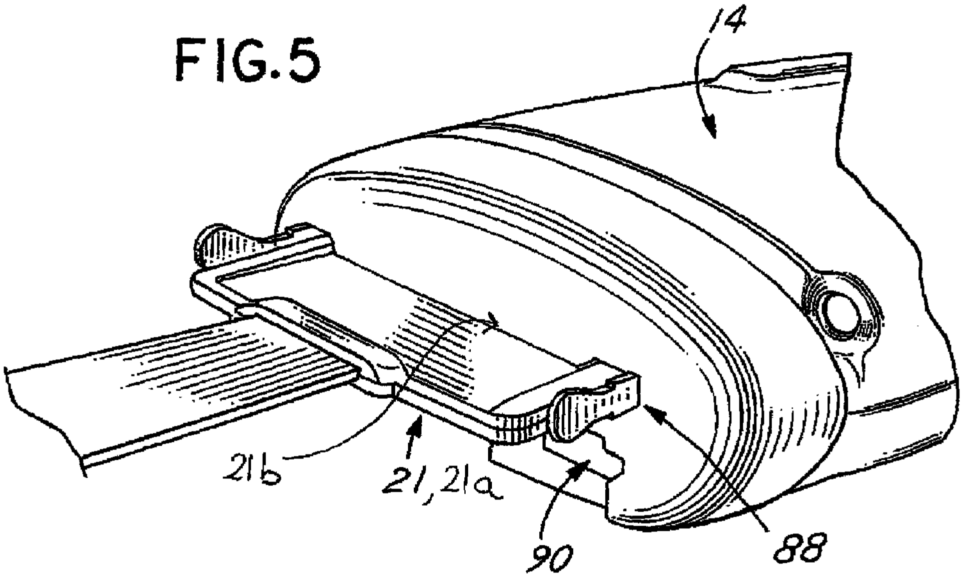
FIG. 5 is a perspective view of an exemplary embodiment of the body electronics unit.

Referring to FIG. 5, the chest assembly 12 connects to the body electronics unit 14 via a chest assembly connector 21. Specifically, the chest assembly connector 21 inserts into a chest assembly port 88 located in the body electronics unit 14. Similarly, the precordial assembly 60 connects to the body electronics unit 14 via the precordial assembly connector 66. Specifically, the precordial assembly connector 66 (not shown) inserts into a precordial assembly port 90. Resisters are connected to the chest assembly port 88 and the precordial assembly port 90 to prevent excessive electrical current from entering the body electronics unit 14—thereby ensuring that the body electronics unit 14 continues to operate properly in the presence a strong electrical current caused by a defibrillator (i.e. a 5 kV defibrillation excitation). The chest assembly connector 21 and the precordial assembly connector 66 are specifically keyed or configured to prevent the assembly connectors 21, 66 from being inserted into the assembly ports 88, 90 backwards, misaligned or otherwise improperly. Moreover, the chest assembly connector 21 is keyed or configured such that it is not compatible with the precordial assembly port 90. Likewise, the precordial assembly connector 66 is keyed or configured such that it is not compatible with the chest assembly port 88. Specifically, as shown in FIG. 5, the chest assembly connector 21 has tongues 21*a* specifically configured or arranged to fit into corresponding grooves 21*b* of the chest assembly port 88. Accordingly, the chest assembly connector 21 can only be connected to the chest assembly port 88 in one orientation. For example, if the tongues 21*a* are not aligned with the grooves 21*b*, the chest assembly connector 21 will not couple to the chest assembly port 88. Likewise, the precordial assembly connector 66 has tongues (not shown) specifically configured or arranged to fit into corresponding grooves (not shown) of the precordial assembly port 90.

Figure 6:
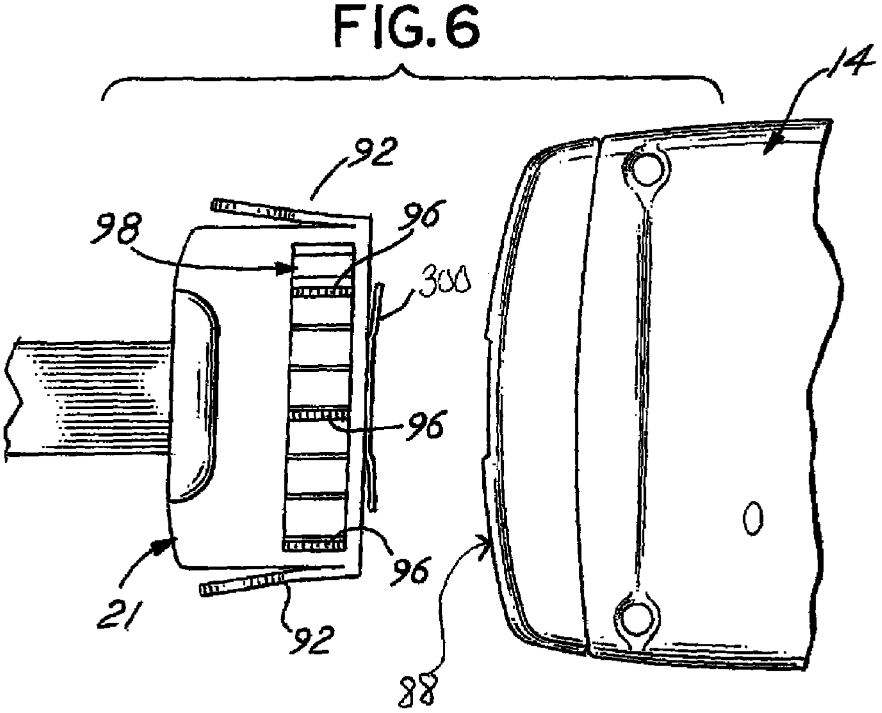
FIG. 6 is a top view an exemplary embodiment of the assembly connectors.

As shown in FIG. 6, the chest assembly connector 21 and the precordial assembly connector 66 (not shown) have retaining clips or flanges 92 located on the sides of the connectors 21, 66 for removably securing the connectors 21, 66 into the assembly ports 88, 90. However, other means may be used to removably secure the connectors 21, 66 in the assembly ports 88, 90, such as screws, pins or the like. In addition, the assembly connectors 21, 66 may have spring flanges or clips 94 located at the tip of the connectors 21, 66 for providing a bias or tension against the assembly ports 88, 90. The spring flanges or clips 94 provide the connectors 21, 66 with a secure fit within the assembly ports 88, 90, thereby reducing any play or movement of the connectors 21, 66 within the assembly ports 88, 90. The electrically conductive elements or traces are specifically configured on the connectors 21, 66 so as to ensure that the electrical signals from the heart are properly transmitted to the body electronics unit 14. In other words, the electrically conductive elements or traces must be sufficiently spaced apart or otherwise isolated in some manner to prevent arcing across the electrically conductive elements. In addition, the spacing of the electrically conductive elements or traces permits the chest assembly and the precordial assembly to withstand defibrillation shock. Furthermore, the connectors 21, 66 have ribs 96 for preventing the electrically conductive elements or traces from coming into contact with metal objects or the like when the connectors 21, 66 are not inserted into the assembly ports 88, 90.

The chest assembly connector 21 has a sensor pin or ground pin 98 that completes a circuit within the body electronics unit 14 when the chest assembly connector 21 is plugged into the chest assembly port 88, thereby activating the power and bringing the body electronic unit 14 out of "sleep mode." The sensor pin has a specific tongue 300 that corresponds and fits into a groove 301 located in the chest assembly port 88 (see FIG. 9B). The sensor pin 98 serves as a means for the body electronics unit 14 to identify the chest assembly 12 and to prevent the use of other chest assemblies or electrocardiograph wearables that are not designed to be used with the on-body electronics unit 14. In other words, the power of the body electronics unit 14 will not activate unless the body electronics unit 14 identifies or recognizes the sensor pin 98 of the chest assembly 12.

Figure 7:
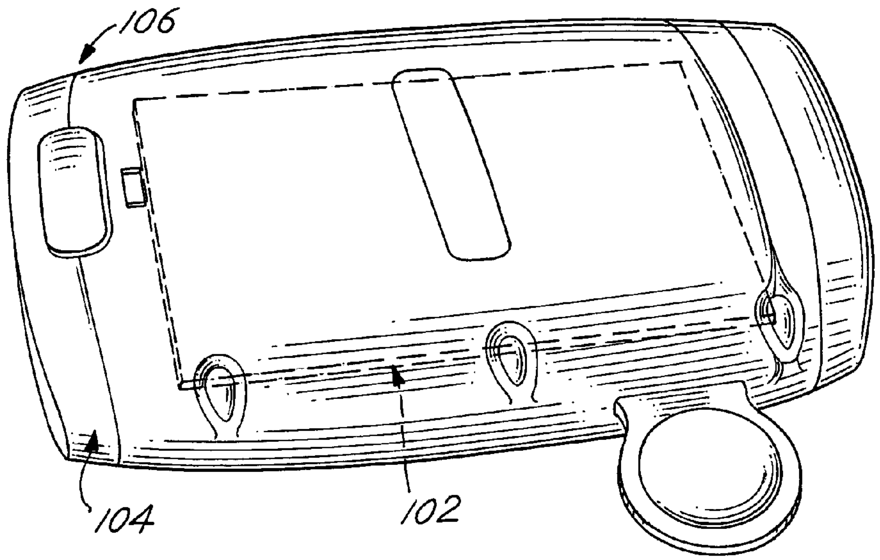
FIG. 7 is a front view of an exemplary embodiment of the body electronics unit.
Figure 7A:
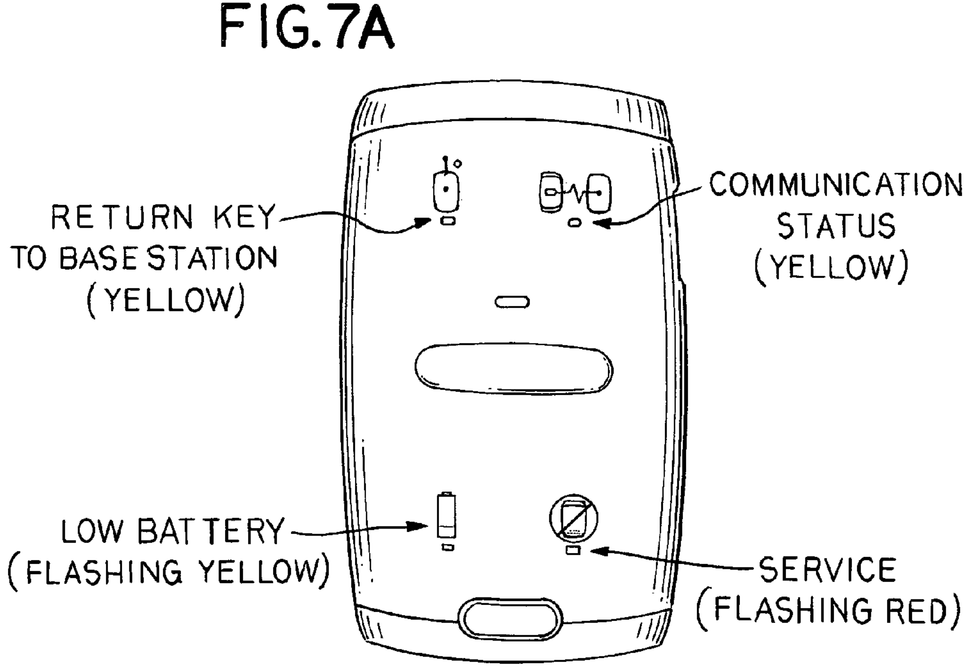
FIG. 7*a* is an exemplary embodiment of the user interface of the electronics body unit.

The outside casing of the body electronics unit 14 is constructed of lightweight, molded plastic, such as acrylonitrile-butadiene-styrene (ABS) or other suitable material. The shape and configuration of the body electronics 14 unit is not limited to any particular shape or configuration. As shown FIG. 1, the body electronic unit 14 removably secures to the patient's arm via an armband 100, thus making the body electronics unit 14 readily accessibly to the patient. The armband 100 wraps around either the patient's right or left arm and attaches via Velcro or other suitable fastening means such as pins, snaps, or the like. The body electronics unit 14 slides under a strap or pocket on the armband 100. Referring to FIG. 7, the body electronic unit 14 has a user interface 102 and a battery 104. The user interface 102 provides information to the patient pertaining to the system's operating status or functionality. For example, an exemplary embodiment of the user interface 102 may provide information on whether the body electronics unit 14 is communicating or transmitting normally to the base station 16, whether the battery 104 of the body electronics unit 14 is charging or the battery 104 is low, whether the power of the body electronics unit 12 is activated, or whether the body electronics unit 14 or base station is malfunctioning. In addition the user interface 102 may provide instructions on the correct order or procedure for pairing or coupling the body electronics unit 14 with the base station 16. Such information may be communicated to the patient via the user interface 102 in various ways, for example, LEDs, LCD, text, audible tones, etc. An exemplary embodiment of the user interface is shown in FIG. 7*a*. The user interface 102 is readily accessible to the patient when the body electronics unit 14 is secured to the armband 100.

The battery 104 is inserted into a battery port 106 located in the bottom of the body electronics unit 14. The battery 104 is retained in the battery port 106 by latches or other suitable fastening means, such as clips, screws or the like. The battery 104 is preferably a 3.6 V Li-ion rechargeable battery. The battery 104 is readily accessible to the patient when the body electronics unit 14 is secured to the armband 100.

The body electronics unit 14 controls the acquisition of the ECG signals from the chest assembly 12 and the precordial assembly 60. A transmitter 108 within the body electronics unit 14 receives or acquires ECG signals from the chest assembly 12 and the precordial assembly 60 preferably at 3 kbps. When the system is operating in "7 lead" mode (i.e. when only the chest assembly 12 is being used) the body electronics unit 14 acquires signals from the RL, RA, LL, LA, and V electrodes. When the system is operating in the "12 lead mode" (i.e. the chest assembly 12 and the precordial assembly 60 are being used) the body electronics unit 14 acquires signals from the RL, RA, LL, and LA electrodes via the chest assembly 12 and acquires signals from the V1 thru V6 electrodes via the precordial assembly 60. In addition, other vital signs of the patient may be detected by the system and transmitted to the body electronics unit 14, for example pulse, respiration rate, heart rate, temperature, EEG signals and pulse oximeter signals.

Figure 8:
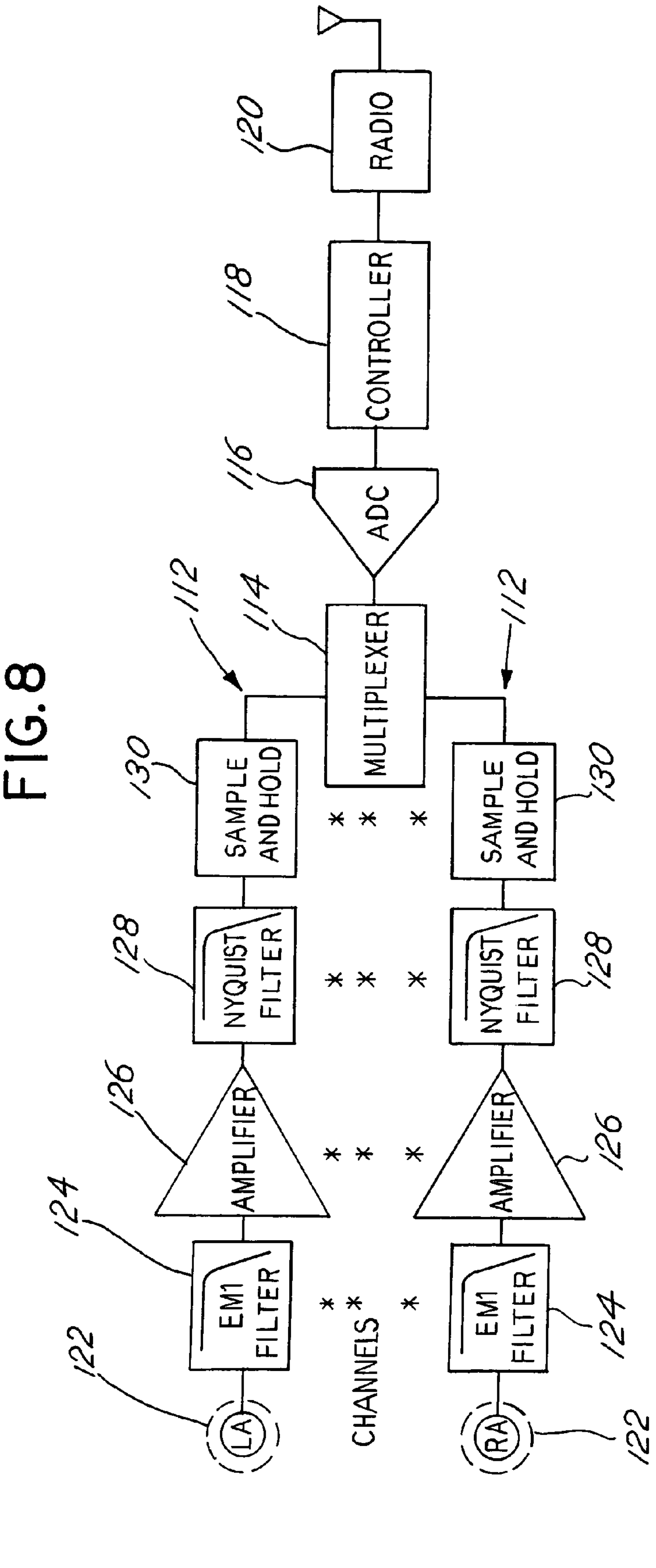
FIG. 8 is a block diagram of an exemplary embodiment of the transmitter.

As shown in FIG. 8, the transmitter 108 comprises an application specific integrated circuit, a processor or other circuit 110, a plurality of signal channels 112, a multiplexer 114, an analog-to digital converter (ADC) 116, a controller 118, and a radio 120. Additionally, fewer or different components can be used. The body electronics unit 14 has nine signal channels 112 corresponding to the ten electrodes connected to the chest assembly 12 and the precordial assembly 60. The electrode channels 112 each comprise a connector 122, a filter 124, an amplifier 126, a Nyquist filter 128 and a track and hold circuit 130. The connectors 122 of the signal channels 112 connect to either the chest assembly port 88 or the precordial assembly port 90, depending on whether the electrode channel 112 corresponds to an electrode located on the chest assembly 12 or the precordial assembly 60. The filter 124 comprises a low pass filter, such as for removing electromagnetic interference signals. The amplifier 126 amplifies the signals from the electrodes. The Nyquist filter 128 comprises a low pass filter for removing out-of-band high frequency content of the amplified signals to avoid sampling error. The track and hold circuit 130 enables the system to sample all nine electrode channels signals 112 at a same or relative times so that there is not differential error created when these signals are combined later in an ECG monitor.

The multiplexer 114 sequentially selects signals from the electrode signal channels 112 using time division multiplexing. One of ordinary skill in the art, however, recognizes that other combination functions can be used. The ADC 116 converts the combined analog signals to digital signals for transmission. Preferably the controller 118 comprises a digital signal processor (DSP) that decimates the digitized signals as to lessen the bandwidth required to transmit the signals. The radio 120 modulates the digital signals with a carrier signal for transmission. In an exemplary embodiment, the radio 120 includes a demodulator for receiving information. The controller 118 digitally transmits the ECG data to the base station 16. In addition to transmitting ECG data, the controller 118 may transmit signals pertaining to pacemaker information, battery level information, electrode disconnection information, and other information as required. For example, vital signs such as pulse, respiration rate, heart rate, temperature, EEG signals, and pulse oximeter signals may be transmitted. .

The body electronics unit continuously monitors the integrity of all patient electrode connections. In the event a lead is disconnected, the body electronics unit will send a signal to the base station which in turn causes the base station to trigger the "lead off" alarm on the ECG monitor. Additionally, the body electronics unit has a self-test function which monitors the integrity of the primary functions including the microprocessor, data acquisition, internal voltage references, and radio functionality. In the event a failure is detected, the body electronics unit will capture the fault condition, stop data acquisition and transmission and indicate that fault has occurred through the lead off alarm.

The body electronics unit 14 operates to minimize undesired noise or signals. For example, components are matched such that later application to a differential amplifier in a legacy ECG monitor for determining a heart vector is accurate. ECG vectors are not formed by the ECG system 10, but rather by the legacy ECG monitor. Because the ECG system 10 is essentially "in-series" with the legacy ECG monitor, any error may produce undesirable results. One potential source of error is differential error. This differential error can be observed on the legacy ECG monitor when the ECG monitor forms the ECG lead signals by combining the individual electrode signals in the ECG monitor input stage. This input stage comprises a difference, or differential, amplifier to eliminate common mode interference from the signals produced at the electrodes 20.

An artifact will be present if there is any difference in how each of the electrode signals are processed when the legacy ECG's differential amplifier forms the ECG lead signals or ECG vectors. For example, if there is a difference in the gain of the amplifier, a difference in the phase shift associated with the anti-aliasing (Nyquist) filters, or a difference in how the respective track and hold circuits treat the electrode signals, then this differential error creates an artifact on the legacy ECG monitor. One important technique to minimize this potential source of differential errors is to choose a Nyquist filter cutoff frequency that is very high. This is because each individual filter will have differing group delay performance. To mitigate that difference, the frequency that this group delay will affect is much higher than the frequency of the ECG signals, which are about 0.05 Hz to 150 Hz. By choosing a high cutoff frequency for the Nyquist filters, any mismatch in the Nyquist filter components will not affect accuracy of the individual electrode ECG signals. For example, picking a filter cutoff frequency of 1,200 Hz mitigates this source of error. With this approach, the individual electrode ECG signals are over sampled at about 3,000 Hz in order to not introduce aliasing. Of course higher filter cutoff frequencies and correspondingly higher sampling rates may further reduce error. Lower cutoff frequencies and/or sampling rate may be used.

Because the electrode signals are now sampled at such a high rate, these signals may be decimated to minimize the required transmission bandwidth. For example the digital samples are decimated by a factor of eight in the controller 118. Greater or lesser rates of decimation can be used, such as decimation as a function of the bandwidth available for transmission, the number of electrode signals to be represented, and the Nyquist sampling rate. Referring back to FIG. 1, the base station 16 receives the transmitted signals sent from the body electronics unit 14. The signals are transmitted as radio or other signals modulated with a carrier signal. Various air-interfaces can be used for transmission, such as the BLUETOOTH protocol or the IEEE 802.11b protocol. To establish proper communication between the body electronics unit 14 and the base station 16, the base station 16 and body electronics unit 14 need to be paired such that the base station 16 and the body electronics unit 14 only recognize signals from the its pair. This may be accomplished in number of ways including direct connection of the base station 16 and the body electronics unit 14. Preferably, a token key 132 is used to pair or radio frequency link the body electronics unit 14 and the base station 16. Referring to FIG. 9*a*, the token key 132 has memory chip and may optionally have a plurality of tongues or pins 133 that fit within grooves located in a token key port 134 of the base station 16 and within grooves of a token key port 136 of the body electronics unit 14. As shown in FIG. 9*b*, the token key 132 inserts into the token key port 134 of the base station and reads and records an identification number for the base station 16. The token key 132 is then removed from the token key port 134 and inserted into the token key port 136 located in the body electronics unit 14. The electronics unit 14 receives the identification number for the base station 16 from the token key 132. In turn, the token key 132 reads and records the identification number for the body electronics unit 14. The token key 132 is then removed from the body electronics unit 14 and reinserted into the token key port 134 of the base station 16 whereby the base station 16 confirms the presence of its own identification number on the token key 132 and also reads the identification number for the body electronics unit 14 from the token key 132. The body electronics unit 14 and the base station 16 are paired. Alternatively, pairing or coupling can be accomplished by first inserting the token key 132 into the body electronics unit 14, removing the token key 132 and inserting the token key 132 into the base station 16, removing the token key 132 and reinserting the token 132 into the body electronics unit 14. In other words, the order in which the token key 132 is inserted into the body electronics unit 14 and the base station 16 is not critical to the proper operation of the system. Referring back to FIG. 7, the user interface 102 may provide the user or health care provider with instructions on the correct order for pairing the body electronics unit 14 with the base station 16. The use of the token key 132 allows the pairing function to occur while the body electronics unit 14 is worn by the patient. This feature eliminates the need to disconnect and reconnect the body electronics unit 14 when a patient needs to be connected to different ECG monitors as a result of being moved around a hospital. The patient's body electronics unit 14 is just repaired with a new base station using the token key 132.

After the body electronics unit 14 and the base station 16 are paired, the body electronics unit 14 and the base station 16 will remain communicating with each other as long as the token key 132 remains in the token key port 134 of the base station 16 (or the token key port 136 of the body electronics unit 14, depending on the order of the pairing process). In other words, as soon as the token key 132 is removed from the base station 16, the electronics unit 14 and the base station 16 will discontinue or cease communication. Any specific token key 132 can be used to pair any specific base station 16 with any specific body electronics unit 14.

Figure 10:
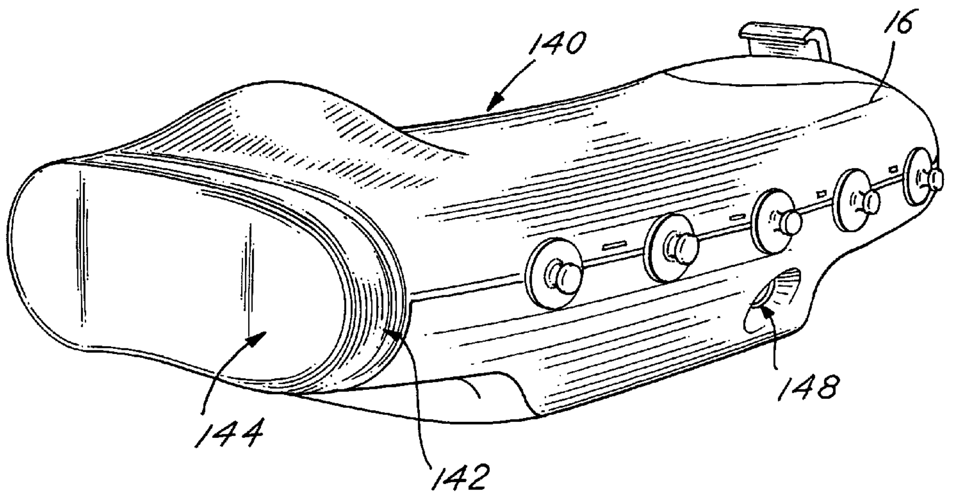
FIG. 10 is a perspective view of an exemplary embodiment of the base station.

The outside casing of the base station 16 is constructed of lightweight, molded plastic, such as acrylonitrile-butadiene-styrene (ABS) or other suitable material. The shape and configuration of the base station 16 is not limited to any particular shape or configuration. The base station 16 is removably secured to an ECG monitor 138 via suitable mounting means, such as Velcro®, dual-lock strips, double-sided foam tape, or the like. Preferably, the base station 16 is removably mounted to a mounting plate secured near the ECG monitor 138 via suitable mounting means. As shown in FIG. 10, the base station 16 has a cradle 140 for storing the body electronics unit 14 when the body electronics unit 14 is not in use or otherwise off the patient. In addition, the base station 16 has a battery port 142 in which a base station battery 144 is removably inserted. The base station 16 may be constructed to have a plurality of battery ports that store and charge batteries when the batteries are not being used. When the base station 16 is not plugged into an AC wall power inlet, the base station battery 144 provides power to the base station 16. When the base station 16 is operating on AC wall power, the base station 16 charges the base station battery 144 when the base station battery 144 is in the battery port 142. The base station 16 has a power switch 146 that activates/deactivates the power to the base station 16 and a power cord connection 148 for connecting a power cord to an AC wall power inlet. The base station battery 144 is preferably a 3.6 V Li-ion rechargeable battery. Accordingly, the base station battery 144 and the body electronics unit battery 104 are preferably identical and interchangeable, such that each battery can be used in either the body electronics unit 14 or the base station 16. The system is designed such that a discharged body electronics unit battery 104 is swapped for a charged base station battery 144. In this manner a charged battery is always readily available for the body electronics unit. In addition, the base station 16 has a lead switch 150 that allows the health care provider to instruct the base station 16 to operate in "7 lead" mode or "12 lead" mode.

Figure 11:
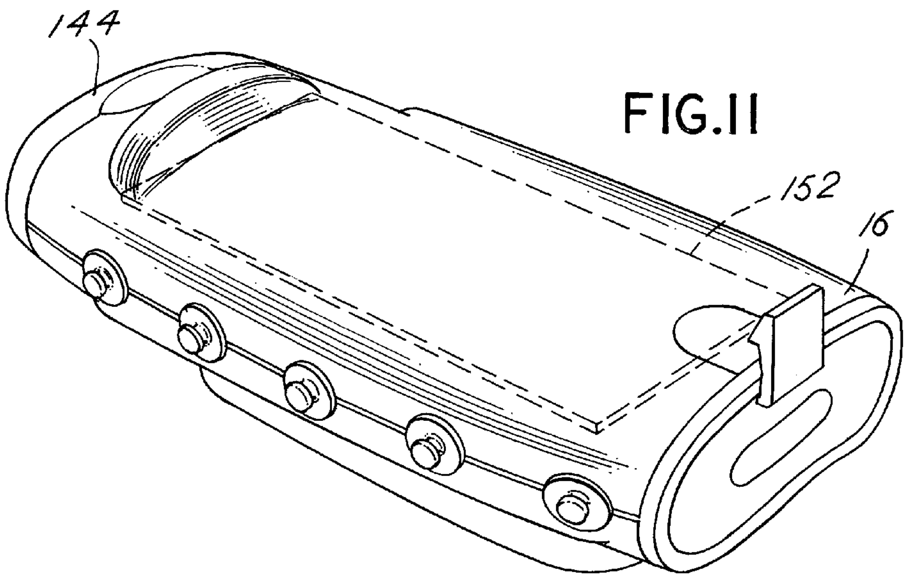
FIG. 11 is a front view of an exemplary embodiment of the base station.
Figure 11A:
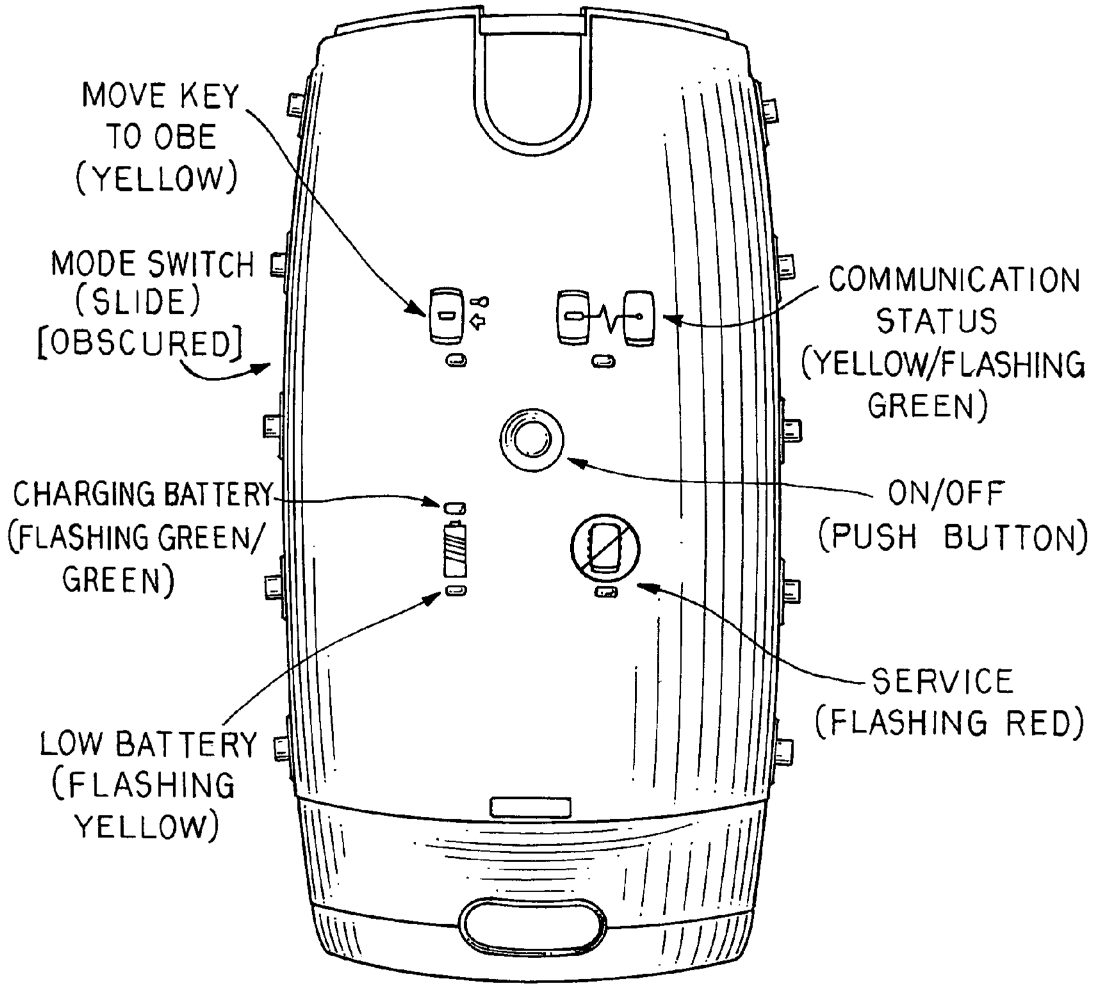
FIG. 11*a* is an exemplary embodiment of the user interface of the base station.

As depicted in FIG. 11, the base station 16 has a user interface 152 that provides information to the health provider or patient pertaining to the system's operating status or functionality. For example, the user interface 152 may provide information on whether the body electronics unit 14 is communicating or transmitting normally to the base station 16, whether the base station battery 144 is charging or the battery 144 is low, whether the body electronics unit battery 104 is low, or whether the power of the base station 16 is activated, whether the base station 16 is malfunctioning or otherwise requires servicing. In addition the user interface 102 may provide instructions on the correct order or procedure for pairing or coupling the body electronics unit 14 with the base station 16. Such information may be communicated to the health care provider or patient via the user interface 152 in various ways, for example, LED's, LCD, text, audible tones, etc. An exemplary embodiment of the user interface 102 is shown in FIG. 11*a*.

Additionally, the base station has a self-test function which monitors the integrity of the primary functions including the microprocessor, data acquisition, internal voltage references, and radio functionality. In the event a failure is detected, the body electronics unit will capture the fault condition, stop data acquisition and transmission and indicate that fault has occurred through the lead off alarm.

Figure 12:
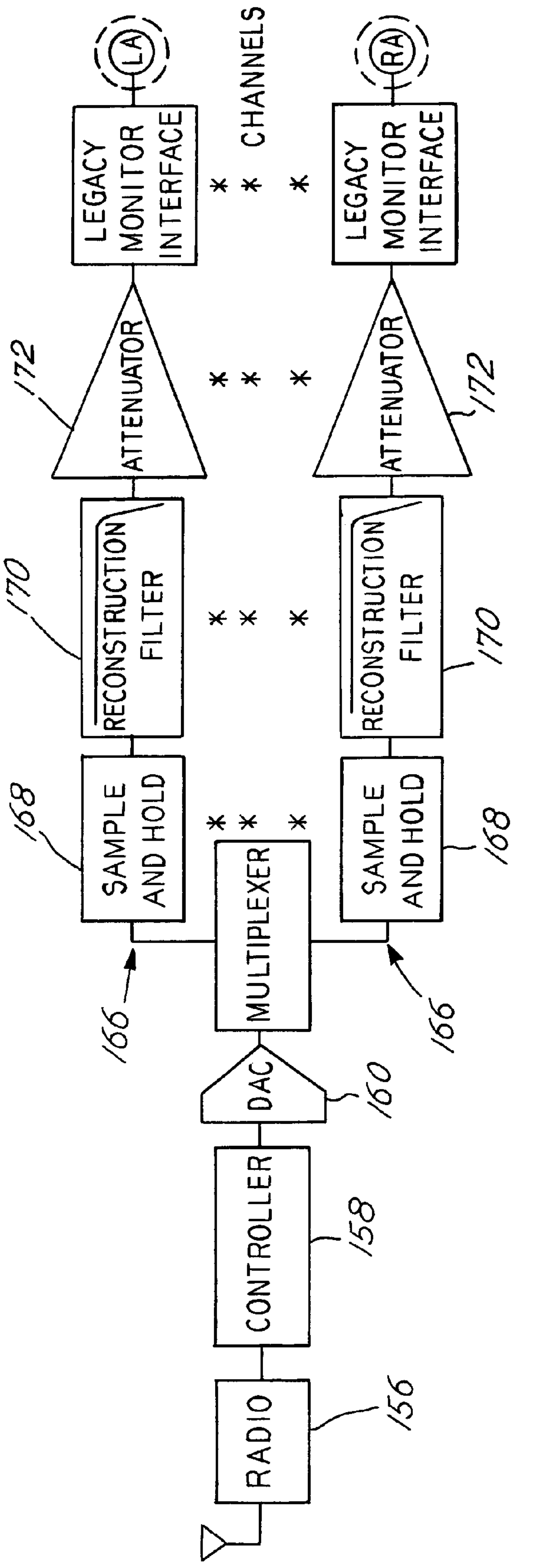
FIG. 12 is a block diagram of an exemplary embodiment of the receiver.

A receiver 154 located within the base station 16 receives signals sent to the base station 16 from the body electronics unit 14. As shown in FIG. 12, the receiver 154 includes a radio 156, a controller 158, a digital-to-analog converter (DAC) 160, a de-multiplexer 162, a transceiver 164, and a plurality of electrode signal channels 166. The radio 156 demodulates the received signals for identifying digital data representing the combined electrode signals. In an exemplary embodiment, the radio 156 includes a modulator for transmitting control information. The controller 158 controls operation of the various components and may further process the signals from the radio 156, such as interpolating data, converting the signals to digital information, generating control signals for the transmitter 108 in the electronics unit 14, operating any user output or input devices, and diagnosing operation of the ECG system. Preferably, the controller 118 interpolates the electrode signals to return the effective sample rate to about 3 kHz or another frequency. This enables the reconstruction filters to have a cutoff frequency many times the bandwidth of the electrode signals, thus minimizing any differences in group delay at the frequencies of interest, i.e. less than 150 Hz. The DAC 160 converts the digital signals to analog signals. The demultiplexer 162 separates the individual regenerated electrode signals onto the separate electrode signal channels 166. The transceiver 164 operates operable pursuant to the BLUETOOTH specification for two-way communication with the transmitter 108.

The receiver 154 has nine electrode signal channels 166 corresponding to the 10 electrodes connected to the chest assembly 12 and the precordial assembly 60. The electrode signal channels 166 each comprise a sample and hold circuit 168, a filter 170, and an attenuator 172. The sample and hold circuit 168 is controlled by the controller 118 so that the converted electrode signals appear simultaneously on each electrode signal channel 166. Other embodiments may include individual DAC's that provide the signal substantially simultaneously. The filter 170 comprises a low pass reconstruction filter for removing high frequency signals associated with the DAC conversion process. The attenuator 172 comprises an amplifier for decreasing the amplitude to a level associated with signals at the electrodes, which were earlier amplified in the amplifiers of the body electronics unit 14. This results in a unity system gain so as not to introduce error between the electrodes and the conventional ECG monitor.

Figure 13:
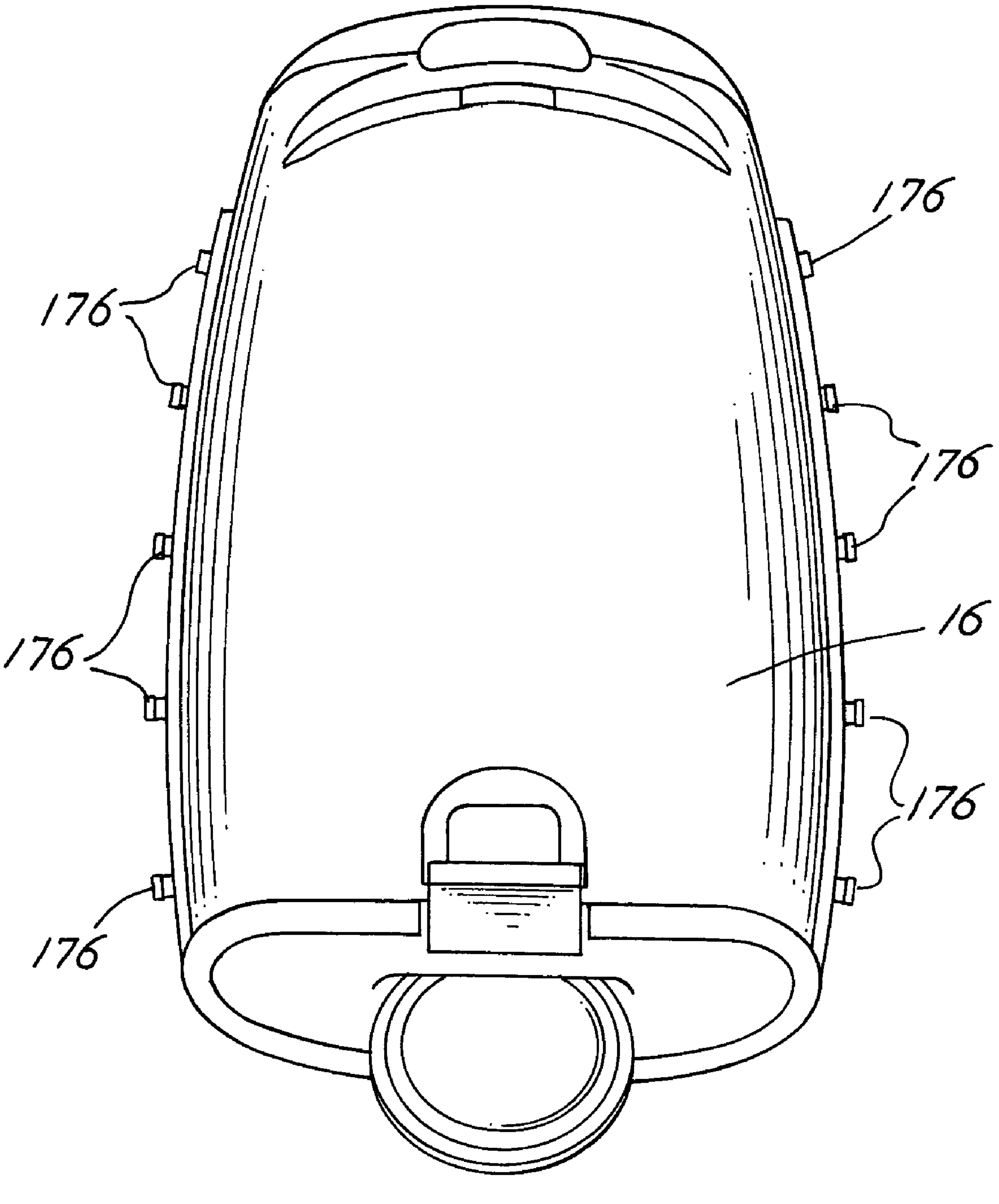
FIG. 13 is a perspective view of an exemplary embodiment of the base station.

The base station 16 transmits the ECG signals to the ECG monitor 138 via pre-existing or conventional monitor cables 174. In turn, the information is displayed on the ECG monitor and reviewed by a physician. As depicted in FIG. 13, the monitor cables 174 removably insert onto snap terminals 176 located on the base station 16. Preferably, the base station 16 has ten snap terminals 176 arranged on the left and right side of the base station 16. The snap terminals 176 and the monitor cables 174 are preferably labeled and color-coded so that the monitor cables 174 are properly connected to the base station 16. For instance, the five snap terminals 176 located on the left side of the base station 16 and the monitor cable 174 may be labeled as RL, LA, LL, RA, and V/V1. In addition, the five snap terminals 176 on the right side of the base station 16 and the monitor cable 174 may be labeled V2, V3, V4, V5, and V6. When the ECG system is operating in "7 lead" mode (i.e. only the chest assembly 12 is used) the monitor cable 174 is plugged into the five snap terminals 176 on the left side of the base station 16. When the ECG system is operating in "12 lead" mode (i.e. both the chest assembly 12 and the precordial assembly 60 is used) both the monitor cables 174 are plugged into the snap terminals 176—the top four snap terminals 176 on the left side of the base station 16 will be used for chest assembly electrodes and the remaining six snap terminals 176 will be used for precordial assembly electrodes.

Figure 15:
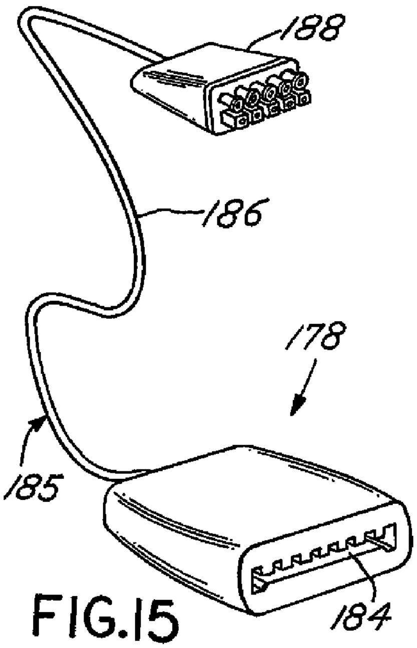
FIG. 15 is another exemplary embodiment of the adaptor assembly.
Figure 14:
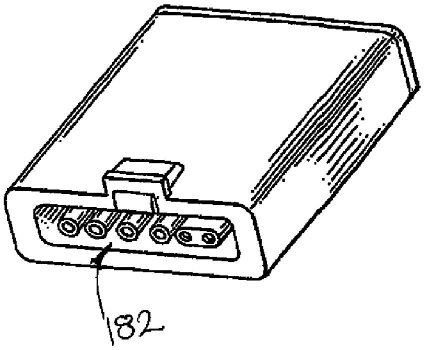
FIG. 14 is an exemplary embodiment of the adaptor assembly.
Figure 16:
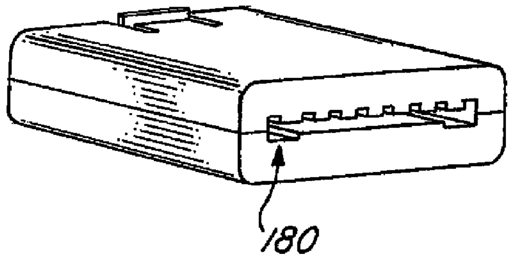
FIG. 16 is another exemplary embodiment of the adaptor assembly.
Figure 16:
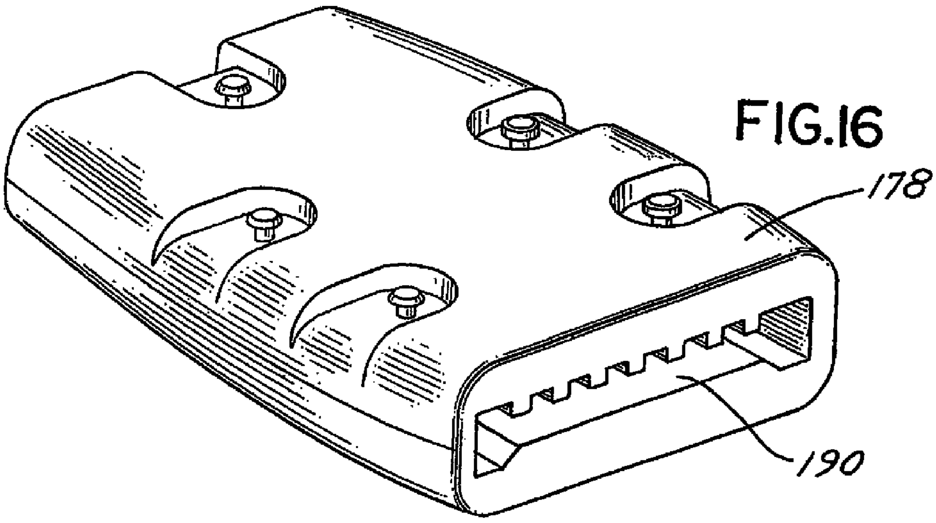

There may be instances where a base station 16 will not be in every ward or hospital room for use with the body electronics unit 14. In such instances, an adapter assembly 178 may be used to connect the chest assembly 12 or the precordial assembly 60 to an ECU monitor 138. In one exemplary embodiment, the adaptor assembly 178 allows the chest assembly 12 or precordial assembly 60 to be plugged directly into a conventional or existing telemetry transmitter. FIG. 14 depicts the adapter assembly 178 having an assembly receptacle 180 that connects to the chest assembly 12 or the precordial assembly 60 and a telemetry box receptacle 182 that connects to a conventional or existing telemetry transmitter. In another exemplary embodiment, the adaptor assembly 178 allows the chest assembly 12 or precordial assembly 60 to be plugged directly into a conventional or existing ECU monitor trunk cables. FIG. 15 depicts the adaptor assembly 178 having an assembly receptacle 184 for connecting to the chest assembly 12 or the precordial assembly 60 and a cable assembly 185 for connecting to a conventional or existing ECU monitor trunk cable. The cable assembly 185 has a cable 186 that connects to a trunk cable adaptor 188 for connecting to an ECU monitor trunk cable. In another exemplary embodiment, the adaptor assembly 178 allows the chest assembly 12 or precordial assembly 60 to be plugged directly into standard lead wires that connect to an ECU monitor. FIG. 16 depicts the adaptor 178 having an assembly receptacle 190 for connecting to the chest assembly 12 or the precordial assembly 60 and a lead wire cable assembly (not shown) for connecting to a lead wire assembly. The cable assembly has a cable (not shown) that connects to a lead wire adaptor (not shown) for connecting to standard lead wires. Various configurations of the adapter 178 are possible depending on the connector configuration of the standard lead wires.

Figure 17:
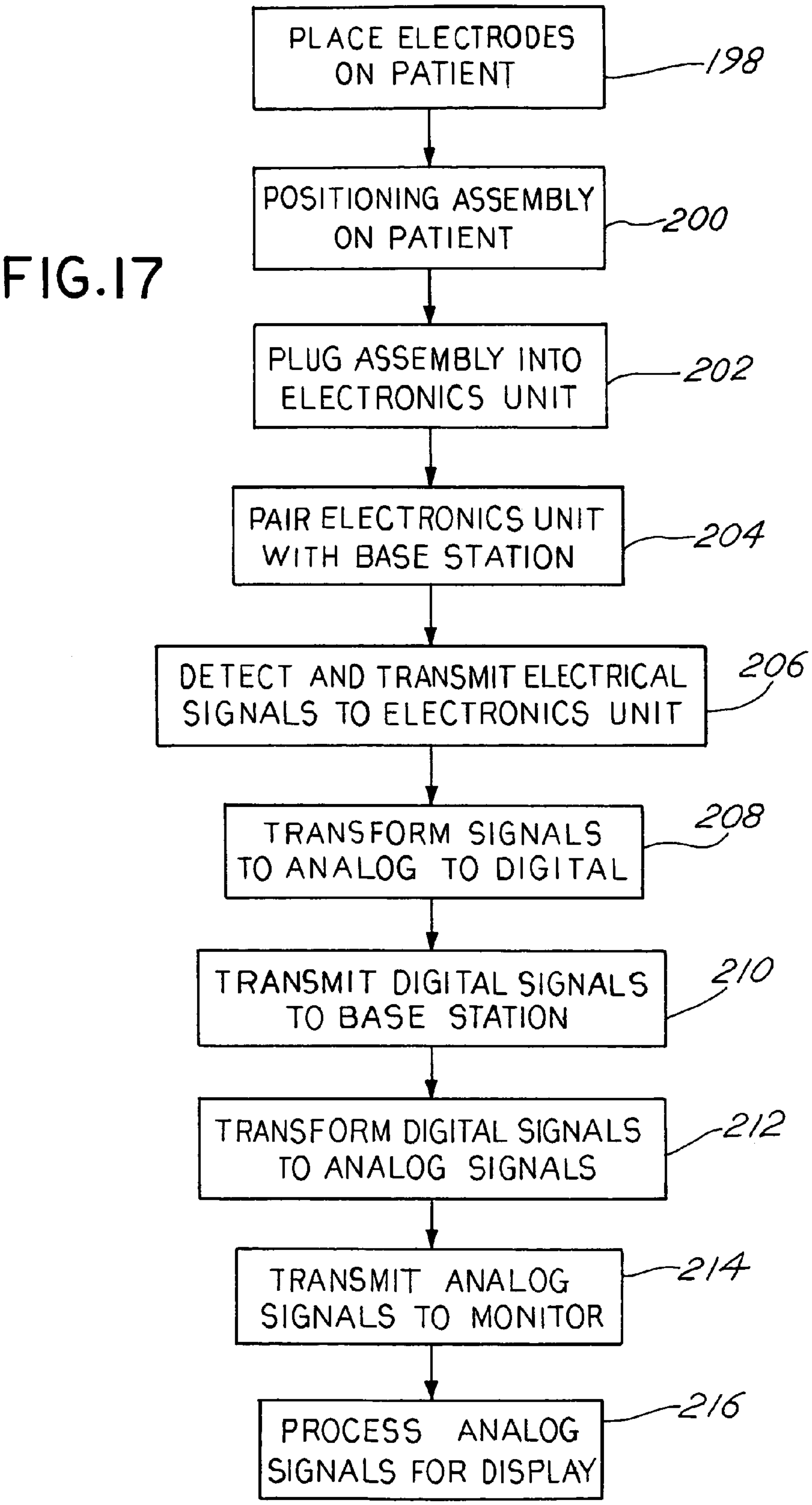
FIG. 17 is a flow chart of an exemplary embodiment for operation of the ECG system.

FIG. 17 depicts the method of monitoring the cardiac activity in the patient's heart using the wireless ECG system of the present invention. In step 198, electrodes are placed on the patient's body. In step 200, the chest assembly 12 and/or precordial assembly 60 are positioned on the patient's body by connecting the electrode connectors 21, 62 to the electrodes. In step 202, the chest assembly 12 and/or the precordial assembly 60 are plugged into the body electronics unit 14. In step 204, the electronics unit 14 and the base station 16 are paired or coupled by inserting the token key 132 into the base station 16, removing the token key 132 from the base station 16, inserting the inserting the token key 132 into the body electronics unit 14, removing the token key 132 from the electronics unit 14, and reinserting the token key 132 into the base station 16. Alternatively, coupling can be accomplished by inserting the token key 132 into the body electronics unit 14, removing the token key 132 from the body electronics unit, inserting the token key 132 into the base station 16, removing the token key 132 from the base station 16 and reinserting the token key 132 into the body electronics unit 14. In step 206, electrical signals from the patient's heart are detected and transmitted to the body electronics unit 14 via chest assembly 12 and the precordial assembly 60. In step 208, the electrical signals from the heart are transformed by the body electronics unit 14 from analog signals to digital signals. In step 210, the body electronics unit 14 transmits the digital signals to the base station 16 via radio transmission. In step 212, the base station 16 transforms the digital signals into analog signals. In step 214, the base station 16 transmits the analog signals to the ECG monitor 138 via monitor cables 174. In step 216, the ECG monitor 138 processes the analog signals into meaningful information that can be displayed on the monitor 138.

In the foregoing specification, the present invention has been described with reference to specific exemplary embodiments thereof. It will be apparent to those skilled in the art, that a person understanding this invention may conceive of changes or other embodiments or variations, which utilize the principles of this invention without departing from the broader spirit and scope of the invention. The specification and drawings are, therefore, to be regarded in an illustrative rather than restrictive sense. Accordingly, it is not intended that the invention be limited except as may be necessary in view of the appended claims.

We claim:

1. An assembly for detecting electrical signals from a patient's heart and conducting those signals to a body electronics unit, comprising:

an electrode retaining section having a plurality of electrode connectors for releasably connecting to conventional metallic or non-metallic electrodes;

an assembly connector attached to the electrode retaining section wherein the electrode retaining section is connected to the assembly connector by a linear section;

a plurality of electrically conductive elements or traces extending between each of said plurality of electrode connectors and said assembly connector;

at least one extension segment selectively contained fully within the electrode retaining section and having an electrode connector that is releasably connected to a conventional metallic or non-metallic electrode;

a plurality of integrated arcuate sections and plurality of transition segments each connected to an electrode connector that is releasably connected to a conventional metallic or non-metallic electrode and contained fully within the electrode retaining section;

a single sensor pin on the assembly connector for completing a circuit within the body electronics unit, wherein the sensor pin has a tongue that corresponds and fits into a groove located in the body electronics unit; and wherein power of the body electronics unit is activated when the sensor pin completes the circuit.

2. The assembly of claim 1 wherein the assembly connector includes a plurality of electrically conductive elements or traces sufficiently spaced to prevent arcing across the electrically conductive elements or traces when subjected to the voltages induced by a defibrillator.

3. The assembly of claim 1 wherein the assembly connector includes at least one spring flange.

4. The assembly of claim 3 wherein the assembly connector includes a plurality of spring flanges.

5. The assembly of claim 4 wherein the spring flanges provide a tension against an assembly port of the body electronics unit to removably secure the assembly connector within the assembly port.

6. The assembly of claim 3 wherein the assembly connector further comprises at least one tongue corresponding to at least one groove in an assembly port of the body electronics unit to removably secure the assembly connector within the assembly port.

7. The assembly of claim 1 wherein the electrically conductive elements or traces are spaced to permit the assembly to withstand a defibrillation shock.

8. The assembly of claim 1 wherein an electrode is positionable about the right side of a patient's chest about level of the first and second intercostal space, an electrode is positionable about the left side of a patient's chest about level of the first and second intercostal space, an electrode is positionable about the middle of a patient's chest about level of the fourth and fifth intercostal space, and two electrodes are positionable about the left side of a patient's torso.

9. The assembly of claim 1 wherein the assembly is mechanically coupled to a telemetry transmitter via an adaptor assembly.

10. The assembly of claim 1 wherein the assembly is mechanically coupled to an electrocardiograph monitor via an adaptor assembly.

11. The assembly of claim 1 wherein a first arcuate section abuts the linear section, a first transition section abuts the first arcuate section and an electrode connector attaches to the first transition segment, the extension arm connects to the first transition section and an electrode connector attaches to the first extension arm, a second arcuate section abuts the first transition section, a second transition section abuts the second arcuate section and an electrode connector attaches to the second transition section, a second extension arm connects to the second transition section and an electrode connector attaches to the second extension arm, a third arcuate section abuts the second transition section, a third transition segment abuts the third arcuate section and an electrode connector attaches to the third transition segment, and a fourth arcuate section abuts the third transition segment and an electrode connector attaches to the fourth arcuate section.

12. An assembly for detecting electrical signals from a patient's heart and conducting those signals to a body electronics unit, comprising:

an electrode retaining section having a plurality of electrode connectors for releasably connecting to conventional metallic or non-metallic electrodes;

wherein the electrode retaining section includes at least one expandable arm having an electrode connector that is releasably connected to a conventional metallic or non-metallic wherein the electrode retaining section further includes an arcuate section, a linear run, and an extension arm;

an assembly connector connected to the electrode retaining section by a linear section;

a plurality of electrically conductive elements or traces extending between each of said plurality of electrode connectors and said assembly connector;

wherein the arcuate section abuts the linear section, a first expandable am attaches to the arcuate section and an electrode connector attaches to the first expandable arm, a transition section abuts the arcuate section and an electrode connector attached to the transition section, a linear run abuts the transition section and an electrode connector attaches to the linear run, and a second expandable arm and an extension arm attach to the linear run, an electrode connector attaches to the second extension arm and an electrode connector attaches to the second expandable arm;

a single sensor pin on the assembly connector for completing a circuit within the body electronics unit, wherein the sensor pin has a tongue that corresponds and fits into a groove located in the body electronics unit; and wherein vower of the body electronics unit is activated when the sensor pin completes the circuit.

13. The assembly of claim 12 wherein a perforated scam extends lengthwise along the extension arm to removably connect the extension arm to the linear run, whereby the extension arm can be selectively positioned on the patient's body when the perforated seam is broken.

14. An assembly for detecting electrical signals from a patient's heart and conducting those signals to a body electronics unit, comprising:

an electrode retaining section having a plurality of electrode connectors for releasably connecting to conventional metallic or non-metallic electrodes;

an assembly connector attached to the electrode retaining section;

a plurality of electrically conductive elements or traces extending between each of said plurality of electrode connectors and said assembly connector;

wherein the assembly connector includes a plurality of ribs to prevent the electrically conductive elements or traces from contacting objects when the assembly connector is not secured within the body electronics unit;

a single sensor pin on the assembly connector for completing a circuit within the body electronics unit, wherein the sensor pin has a tongue that corresponds and fits into a groove located in the body electronics unit; and wherein power of the body electronics unit is activated when the sensor pin completes the circuit.

* * * * *